(12) United States Patent
Fuchs et al.

(10) Patent No.: US 11,058,724 B2
(45) Date of Patent: Jul. 13, 2021

(54) METHODS OF USING DNASE1-LIKE 3 IN THERAPY

(71) Applicant: Neutrolis, Inc., Cambridge, MA (US)

(72) Inventors: Tobias A. Fuchs, Wellesley, MA (US); Abdul Hakkim R., Cambridge, MA (US)

(73) Assignee: NEUTROLIS, INC., Cambridge, MA (US)

(*) Notice: Subject to any disclaimer, the term of this patent is extended or adjusted under 35 U.S.C. 154(b) by 0 days.

(21) Appl. No.: 16/915,547

(22) Filed: Jun. 29, 2020

(65) Prior Publication Data

US 2020/0323917 A1 Oct. 15, 2020

Related U.S. Application Data

(63) Continuation-in-part of application No. 16/697,502, filed on Nov. 27, 2019, now Pat. No. 10,988,746, which is a continuation of application No. PCT/US2019/055178, filed on Oct. 8, 2019.

(60) Provisional application No. 62/846,904, filed on May 13, 2019, provisional application No. 62/808,601, filed on Feb. 21, 2019, provisional application No. 62/779,104, filed on Dec. 13, 2018, provisional application No. 62/775,563, filed on Dec. 5, 2018, provisional application No. 62/742,682, filed on Oct. 8, 2018, provisional application No. 62/978,976, filed on Feb. 20, 2020.

(51) Int. Cl.
| | | |
|---|---|---|
| *A61K 35/17* | (2015.01) | |
| *C12N 15/86* | (2006.01) | |
| *C12N 9/22* | (2006.01) | |
| *C07K 14/76* | (2006.01) | |

(52) U.S. Cl.
CPC .............. *A61K 35/17* (2013.01); *C07K 14/76* (2013.01); *C12N 9/22* (2013.01); *C12N 15/86* (2013.01); *C07K 2319/00* (2013.01)

(58) Field of Classification Search
CPC .... A61K 35/17; C07K 14/76; C07K 2319/00; C12N 15/86; C12N 9/22
See application file for complete search history.

(56) References Cited

U.S. PATENT DOCUMENTS

| | | | |
|---|---|---|---|
| 6,482,626 B2 | 11/2002 | Baker et al. | |
| 6,656,685 B2 | 12/2003 | Utermohlen et al. | |
| 7,612,032 B2 | 11/2009 | Genkin et al. | |
| 8,388,951 B2 | 3/2013 | Genkin et al. | |
| 8,431,123 B2 | 4/2013 | Genkin et al. | |
| 8,535,663 B2 | 9/2013 | Genkin et al. | |
| 8,796,004 B2 | 8/2014 | Genkin et al. | |
| 8,916,151 B2 | 12/2014 | Genkin et al. | |
| 9,072,733 B2 | 7/2015 | Genkin et al. | |
| 9,149,513 B2 | 10/2015 | Bartoov et al. | |
| 9,198,957 B2 | 12/2015 | Ratner et al. | |
| 9,205,133 B2 | 12/2015 | Dawson et al. | |
| 9,248,166 B2 | 2/2016 | Gerkin et al. | |
| 9,402,884 B2 | 8/2016 | Burns | |
| 9,642,822 B2 | 5/2017 | Wagner | |
| 9,770,492 B2 | 9/2017 | Genkin et al. | |
| 9,845,461 B2 | 12/2017 | Genkin et al. | |
| 9,867,871 B2 | 1/2018 | Jain | |
| 2004/0138156 A1 | 7/2004 | Schneider et al. | |
| 2009/0010966 A1 | 1/2009 | Davis et al. | |
| 2013/0149749 A1 | 6/2013 | Holliger et al. | |
| 2016/0251638 A1 | 9/2016 | Posada et al. | |
| 2016/0376366 A1 | 12/2016 | Chang et al. | |
| 2020/0024585 A1 | 1/2020 | Fuchs et al. | |

FOREIGN PATENT DOCUMENTS

| | | | |
|---|---|---|---|
| WO | 2011053982 | | 5/2011 |
| WO | 2011131772 | | 10/2011 |
| WO | 2018015474 | | 1/2018 |
| WO | WO 2018/064681 | * | 4/2018 |
| WO | 2018134403 | | 7/2018 |
| WO | 2018134419 | | 7/2018 |
| WO | 2019036719 | | 2/2019 |

OTHER PUBLICATIONS

Rodriguez et al., GenBank accession No. Q13609 Sep. 27, 2017.*
Ensembl ID No. ENSG00000163687, release 102, Nov. 2020.*
Andersen et al. 2014; Extending serum half-life of albumin by engineering neonatal Fc receptor (FcRn) binding. Journal of Biological Chemistry. 289(19): 13492-13502.
Napirei et al. 2009; Murine serum nucleases—contrasting effects of plasmin and heparin on the activities of DNase1 and DNase1-lie 3 (DNase113). FEBS Journal. 276: 1059-1073.
Shiokawa et al. 2003; Identification of two functional nuclear localization signals in DNase gamma and their roles in its apoptotic DNase activity. Biochem. J. 376: 377-381.
Berntsson et al., "Structural insight into DNA binding and oligomerization of the multifunctional Cox protein of bacteriophage P2", Nucleic Acids Research, vol. 42, No. 4, 2014, pp. 2725-2735.
Hakkim et al., "Impairment of neutrophil extracellular trap degradation is associated with lupus nephritis", PNAS, vol. 107, No. 21, 2010, pp. 9813-9818.
International Search Report and Written Opinion for International Application No. PCT/US2018/047084 , dated Feb. 15, 2019, 23 pages.

(Continued)

*Primary Examiner* — Delia M Ramirez
(74) *Attorney, Agent, or Firm* — Morgan, Lewis & Bockius LLP

(57) ABSTRACT

The present disclosure provides D1L3 enzymes having complete or partial C-terminal deletions of the basic domain (BD), which have substantially enhanced chromatin-degrading activity. In various aspects, the invention provides chromatinase enzyme therapy, which is optionally provided by delivering polynucleotides encoding chromatinases such as D1L3, or by delivering host cells expressing and secreting the same.

18 Claims, 21 Drawing Sheets

Specification includes a Sequence Listing.

(56) References Cited

OTHER PUBLICATIONS

Keyel, "Dnases in health and disease", Developmental Biology, vol. 429, 2017, pp. 1-11.

Kobayashi et al., "Synchronous Growth of Pichia Pastoris for a High-Rate Production of DNaseI at Microquantities", Department of Chemical Engineering. Toyko Institute of Technology. On-Line No. 833, 2004 pp. 1-6.

Perini et al., "Topical application of Acheflan on rat skin injury accelerates wound healing: a histopathological, immunohistochemical and biochemical study", BMC Complementary and Alternative Medicine, 2015, vol. 15, No. 203, pp. 1-8.

Piccolo et al., "Intrapleural Tissue Plasminogen Activator and Deoxyribonuclease for Pleural Infection; An Effective and Safe Alternative to Surgery", AnnalsATS, vol. 11, No. 9, 2014, pp. 1419-1425.

Sisirak et al., "Digestion of Chromatin in Apoptotic Cell Microparticles Prevents Autoimmunity", Cell vol. 166, 2016, pp. 88-101.

Wilber et al., "Deoxyribonuclease I-like III is an Inducible Macrophage Barrier to Liposomal Transfection", MolecularTherapy, vol. 6, No. 1, 2002, pp. 35-42.

Jiménez-Alcázar et al., "Host DNases prevent vascular occlusion by neutrophil extracellular traps," Science 358, pp. 1202-1206 (2017).

Branden et al., "Prediction, Engineering, and -Design of Protein Structures", Introduction to Protein Structure, Garland Publishing Inc., New York, p. 247, 1991.

Seffernick, et al., "Melamine deaminase and Atrazine Chlorohydrolase: 98 Percent Identical but Functionally Different", Journal of Bacteriology, 2001, pp. 2405-2410.

Shiokawa et al., "Characterization of Human DNase I Family Endonucleases and Activation of DNase γ during Apoptosis", Biochemistry 2001, 40, pp. 143-152.

Tang et al., "Identification of Dehalobacter Reductive Dehalogenases that Catalyse Dechlorination of Chloroform, 1,1,1-trichloroethane and 1,1-dichloroethane", Phil Trans R Soc B, 368, Mar. 18, 2012, 1-10, 2013.

Witkowski et al., "Conversion of a β-Ketoacyl Synthase to a Malonyl Decarboxylase by Replacement of the Active-Site Cysteine with Glutamine", Biochemistry 1999, 38, pp. 11643-11650.

Sadowski et al., "The sequence-structure relationship and protein function prediction", Current Opinion in Structural Biology 19:357-362, 2009.

Baron et al., Cloning and characterization of an actin-resistant DNase I-like endonuclease secreted by macrophages, Gene, 1998, vol. 215 pp. 291-301.

Saito et al., Apoptotic DNA endonuclease (DNase-γ) gene transfer induces cell death accompanying DNA fragmentation in human glioma cells, Journal of Neuro-Oncology, 2003, vol. 63, pp. 25-31.

Onuora, "DNASE1L3 prevents anti-DNA responses", Nature Rev. Rheumatol., 2016, vol. 12 No. 437, 1 page.

Wang et al., "Targeting the extracellular scavenger DNASE1L3 on SLE", J Xiangya Med, 2017, 3 pages.

Barnes et al. "Targeting potential drivers of COVID-19: Neutrophil extracellular traps", J. Exp. Med., 2020, vol. 217, pp. 1-7.

Al-Mayouf et al., Loss-of-function variant in DNASE1L3 causes a familial form of systemic lupus erythematosus, Nature Genetics, 2011, vol. 43, No. 12, pp. 1186-1188.

Özçakar et al., DNASE1L3 Mutations in Hypocomplementemic Urticarial Vasculitis Syndrome, Arthritis & Rheumatism, 2013, vol. 65, No. 8, pp. 2183-2189.

Carbonella et al., An autosomal recessive DNASE1L3-related autoimmune disease with unusual clinical presentation mimicking systemic lupus erythematosus, Lupus, 2017, vol. 26, pp. 768-772.

Bruschi et al., Neutrophil extracellular traps (NET) induced by different stimuli: A comparative proteomic analysis, Plos One, 2019, pp. 1-18.

Landhuis, "Spider-Man' Immune Response May Promote Severe COVID-19", Sci. Am., 2020, pp. 1-7.

Reizis, "Project 3: The role of DNASE1L3 and its DNA substrate in lupus", National Institute of Health (NIH), 2015, 5 pages.

\* cited by examiner

FIG. 3

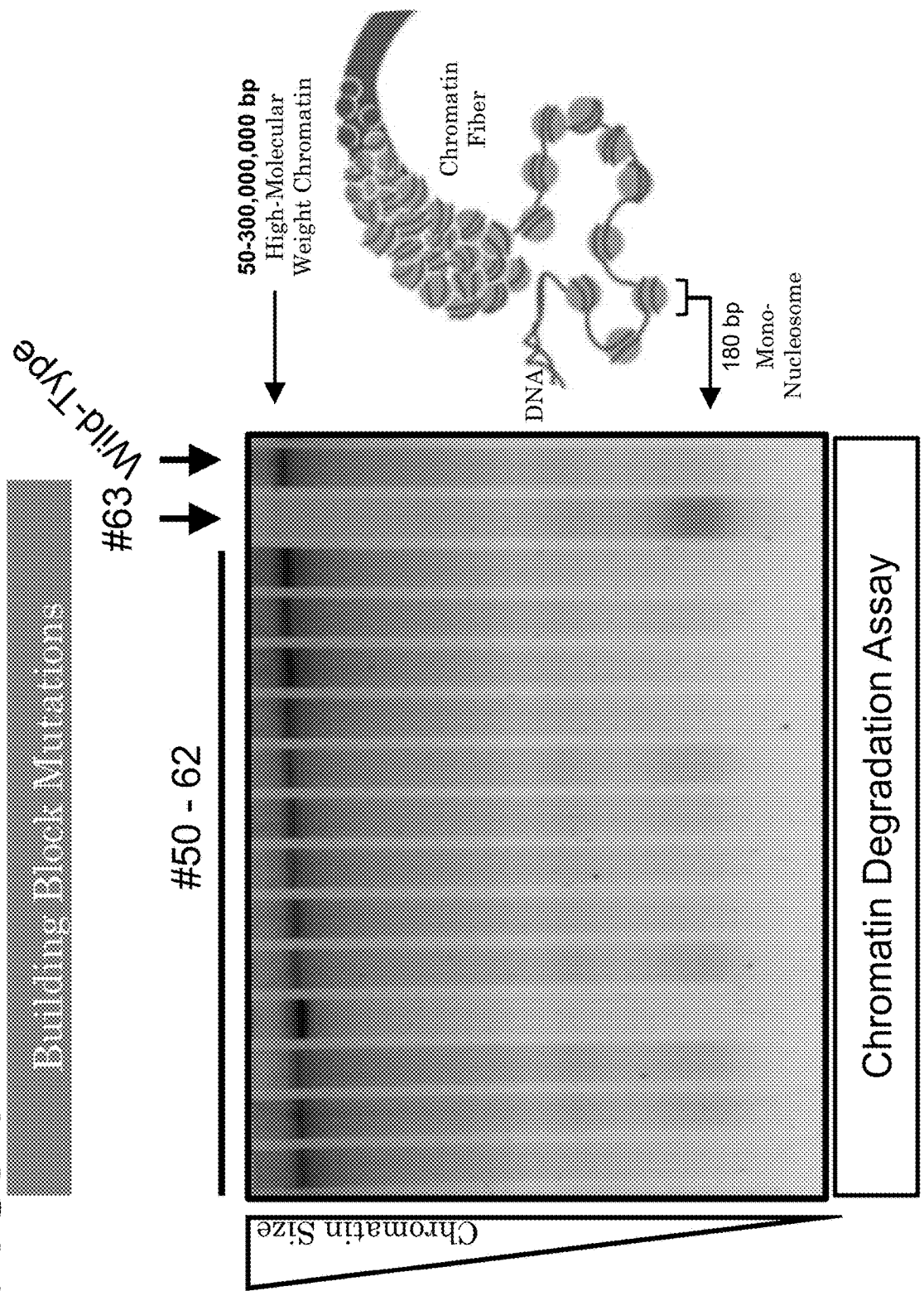

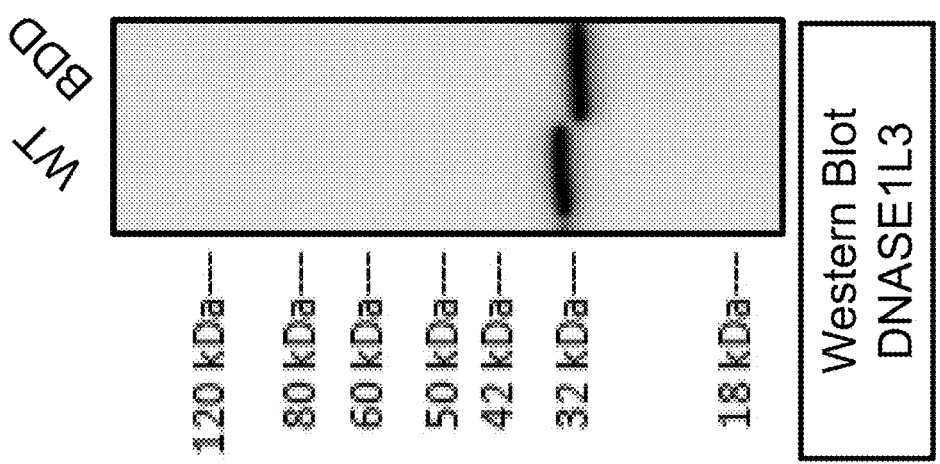

FIG. 6

| Amino Acid Position | | 290 | 300 | # Of Deleted Amino Acids |
|---|---|---|---|---|
| Wild-Type | KLQSS | RAFTNS | KKSVTLRKKTKSKRS | 0 |
| S305del | KLQSS | RAFTNS | KKSVTLRKKTKSKR- | 1 |
| K303_S305del | KLQSS | RAFTNS | KKSVTLRKKTKS--- | 3 |
| V294_S305del | KLQSS | RAFTNS | KKS------------ | 12 |
| K291_S305del | KLQSS | RAFTNS | --------------- | 15 |
| R285_S305del | KLQSS | ------ | --------------- | 21 |
| S283_S305del | KLQ-- | ------ | --------------- | 23 |

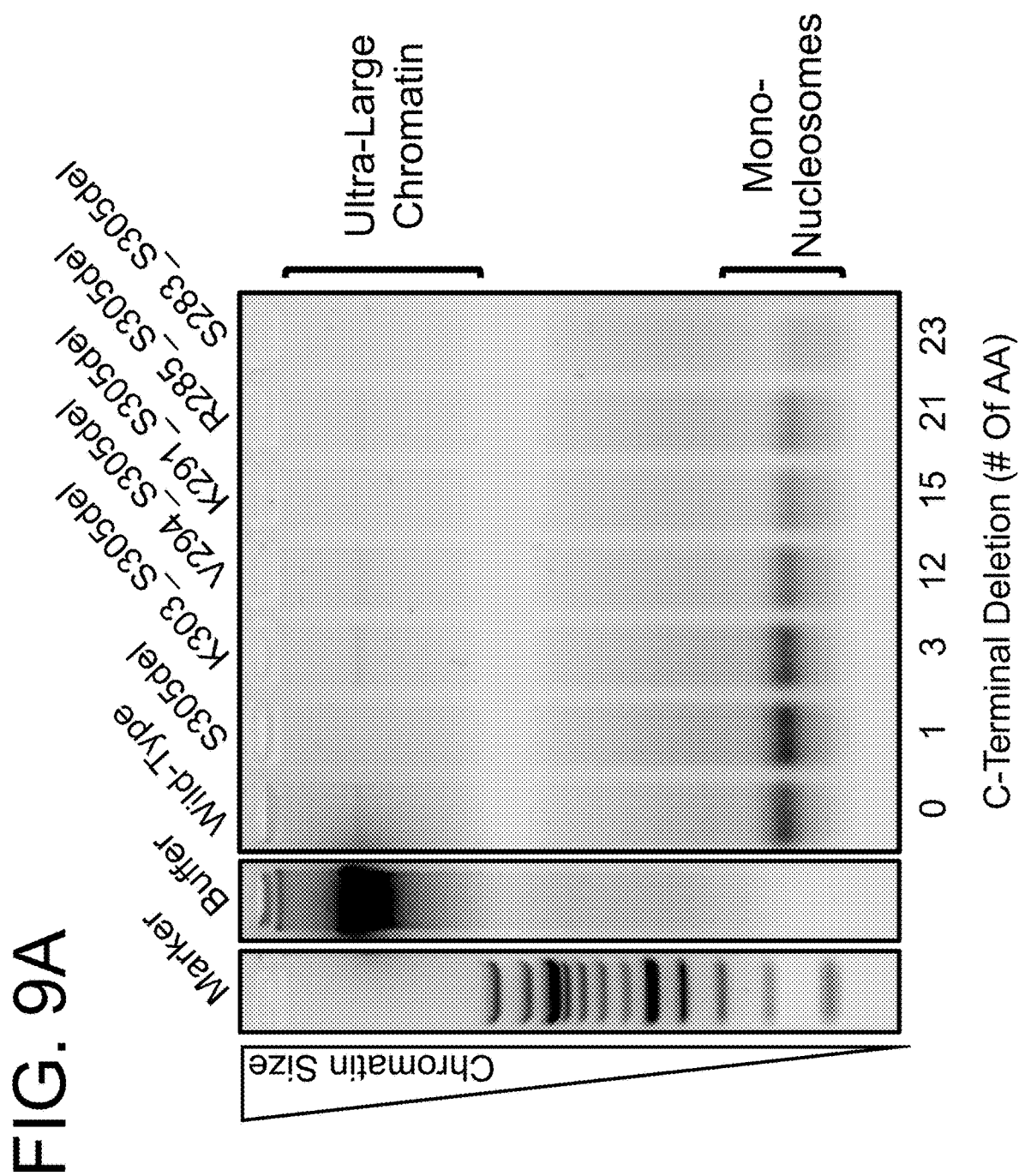

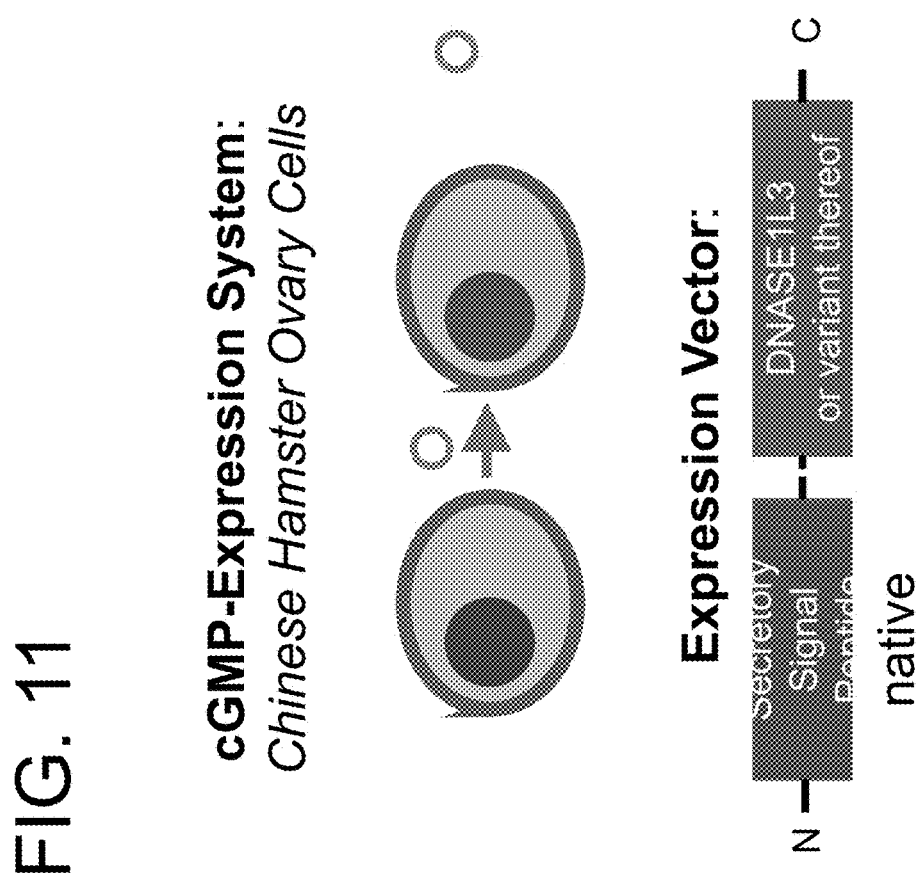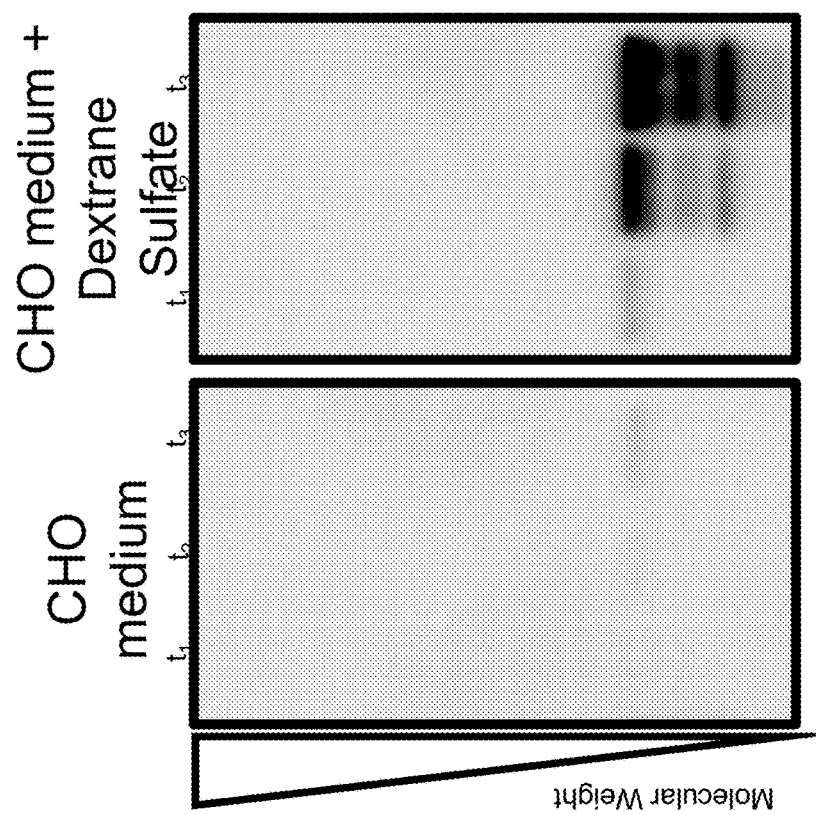
FIG. 11

FIG. 12A
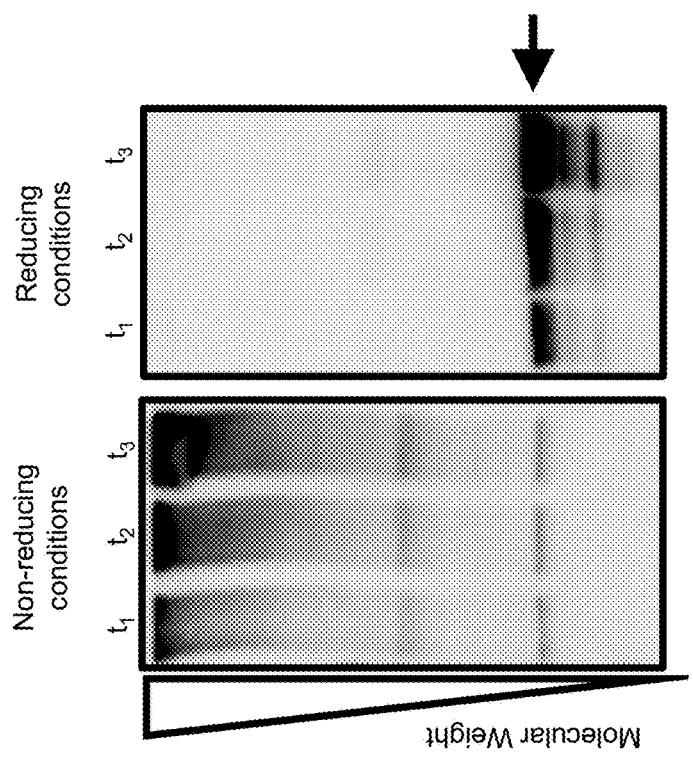
FIG. 12B
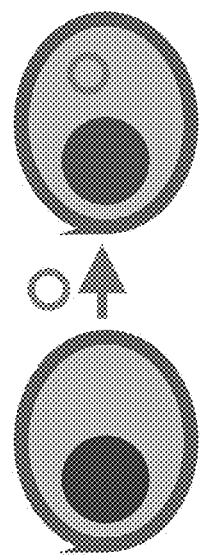 

FIG. 14

| Amino Acid Position | 280 ... 290 ... 300 ... | # Of Deleted Amino Acids |
|---|---|---|
| Wild-Type    | KLQSSRAFTNSKKSVTLRKKTKSKRS | 0 |
| S305del      | KLQSSRAFTNSKKSVTLRKKTKSKR- | 1 |
| K303_S305del | KLQSSRAFTNSKKSVTLRKKTKS--- | 3 |
| V294_S305del | KLQSSRAFTNSKKS------------ | 12 |
| K291_S305del | KLQSSRAFTNS--------------- | 15 |
| R285_S305del | KLQSS--------------------- | 21 |
| S283_S305del | KLQ----------------------- | 23 |

Uniprot: Q13609

T-Cells Do Not Express DNASE1L3

METHODS OF USING DNASE1-LIKE 3 IN THERAPY

PRIORITY

This application is a continuation-in-part of U.S. application Ser. No. 16/697,502, filed Nov. 27, 2019, which is a continuation of International Application No. PCT/US2019/055178, filed Oct. 8, 2019, which claims the benefit of: U.S. Provisional Application No. 62/846,904, filed May 13, 2019; U.S. Provisional Application No. 62/808,601, filed Feb. 21, 2019; U.S. Provisional Application No. 62/779,104, filed Dec. 13, 2018; U.S. Provisional Application No. 62/775,563, filed Dec. 5, 2018; and U.S. Provisional Application No. 62/742,682, filed Oct. 8, 2018, each of which is hereby incorporated by reference in its entirety. This Applications further claims the benefit of U.S. Provisional Application No. 62/978,976, filed Feb. 20, 2020, which is hereby incorporated by reference in its entirety.

BACKGROUND

Inflammation is an essential host response to control invading microbes and heal damaged tissues. Uncontrolled and persistent inflammation causes tissue injury in a plethora of inflammatory disorders. Neutrophils are the predominant leukocytes in acute inflammation. During infections, neutrophils generate neutrophil extracellular traps (NETs), lattices of DNA-filaments decorated with toxic histones and enzymes that immobilize and neutralize bacteria. However, inappropriately released NETs may harm host cells due to their cytotoxic, proinflammatory, and prothrombotic activity.

Two endogenous extracellular DNA-degrading enzymes, DNASE1 (D1) and DNASE1-LIKE 3 (D1L3), limit collateral damage during homeostatic inflammatory responses. D1 and D1L3 are evolutionarily conserved and found in a variety of species including, humans, primates, and rodents. D1 is predominantly expressed in the gastrointestinal tract and exocrine glands, whereas hematopoietic cells, namely macrophages and dendritic cells produce D1L3. While D1L3 has much higher activity for degrading extracellular chromatin and NETs (as compared to D1, which has little to no chromatin-degrading activity), wild-type D1L3 does not have the physical, enzymatic, or pharmacodynamic properties suitable for enzyme replacement therapy.

Therapies providing high DNA- or chromatin-degrading activity are needed for treating conditions characterized by pathological accumulation of extracellular chromatin, including NETs.

SUMMARY

D1L3 features a 23-amino acid long C-terminal tail, which contains 9 basic amino acids and is thus known as the Basic Domain (BD). The BD is unique to DTL3 and is not present in D1. The BD contains a nuclear localization signal (NLS) that targets the enzyme to the nucleus during apoptosis. While it has been widely considered that the BD is critical for the biologic activity of D1L3 in the extracellular space, this disclosure surprisingly shows that deletion of the C-terminal tail in fact stimulates chromatinase activity of D1L3. In accordance with aspects of the invention, the D1L3 enzymes described herein are more suitable and/or effective for therapy and/or are more amenable to large-scale manufacturing. The D1L3 enzymes disclosed herein have benefits for systemic therapy. Such benefits include longer exposure (e.g., slower elimination, longer circulatory half-life), extended duration of pharmacodynamic action, and improved chromatin-degrading activity.

In various embodiments, the invention provides a DNASE1-LIKE 3 (D1L3) enzyme comprising an amino acid sequence that has at least 70% sequence identity to D1L3 Isoform 1 (SEQ ID NO:4) or D1L3 Isoform 2 (SEQ ID NO:5) lacking the BD, and wherein the D1L3 enzyme has a deletion of at least three amino acids from the BD. Amino acid deletions of the Basic Domain of D1L3 improve its chromatin-degrading activity. Further, increasing deletions of the 23-amino acid BD directly correlate with increasing chromatin-degrading activity, including activity for degrading mono-nucleosomes.

Amino acid deletions of the BD can be anywhere in the BD. For example, deletions can be independently selected from the N-terminal side of the BD, from the C-terminal side of the BD, and internal to the BD. In some embodiments, one or more amino acid deletions are within the NLS of the BD.

In some embodiments, the D1L3 enzyme is fused to a carrier protein, optionally by means of an amino acid linker. The carrier protein is generally a half-life extending moiety, such as albumin, transferrin, an Fc, or elastin-like protein, or a variant thereof.

In some embodiments, the D1L3 enzyme is fused to an albumin amino acid sequence or domain. Albumin can be joined to the D1L3, optionally with an interposed linker, at the N-terminus and/or the C-terminus of the D1L3 enzyme. In some embodiments, the D1L3 enzyme comprises an albumin sequence fused to the N-terminus of the mature D1L3 enzyme with an interposed amino acid linker. The peptide linker may be a flexible linker, a rigid linker, or in some embodiments a physiologically-cleavable linker. An exemplary fusion protein for use in systemic therapy is represented by SEQ ID NO: 47, which includes an N-terminal albumin amino acid sequence, a flexible linker of 31 amino acids, and a mature D1L3 amino acid sequence having a full deletion of the BD.

In still other aspects, the invention provides a DNASE-LIKE 3 (D1L3) enzyme comprising an amino acid sequence that has at least 70% sequence identity to D1L3 Isoform 1 (SEQ ID NO:4) or D1L3 Isoform 2 (SEQ ID NO:5), and wherein the D1L3 enzyme has a single amino acid truncation of the BD. D1L3 enzymes having a single amino acid truncation from the BD have surprisingly high DNase activity.

The invention in some aspects provides pharmaceutical compositions comprising the D1L3 enzyme described herein, or optionally a polynucleotide encoding the D1L3 enzyme, or a transfection or expression vector comprising the same, and a pharmaceutically acceptable carrier. The pharmaceutical composition may be formulated for any administration route, including topical, parenteral, or pulmonary administration.

In some aspects, the invention provides mammalian host cells (e.g., human host cells), as well as methods of making and using the same. The host cells comprise a heterologous polynucleotide encoding a chromatinase enzyme operably linked to a promoter. The host cells delivered to a subject express and secrete the encoded chromatinase enzyme. In these aspects, challenges in manufacturing chromatinases such as D1L3 at large scale are avoided. Further, by expressing and delivering D1L3 through heterologous expression in a white blood cell such as a T cell, D1L3 therapy can be localized in part to areas of inflammation or tissue destruction or cell apoptosis. Further, since D1L3 has a circulation half-life of less than about 30 minutes, the cell therapy described herein provides for a sustained therapy, with as few as one, two, three, or four treatments in some embodiments. In some embodiments, the therapy is provided to a subject for treatment of cancer (e.g., leukemia) or viral infection, including infection of the lower respiratory tract.

In other aspects, the invention provides a method for treating a subject in need of extracellular DNA or chromatin degradation, extracellular trap (ET) degradation and/or neutrophil extracellular trap (NET) degradation. The method comprises administering a therapeutically effective amount of the D1L3 enzyme or composition described herein (including host cell compositions). In various embodiments, the present invention provides a method for treating, preventing, or managing diseases or conditions characterized by the presence or accumulation of NETs or extracellular chromatin.

In certain embodiments, the present invention pertains to the treatment of diseases or conditions characterized by deficiency of D1L3, or a deficiency of D1. In some cases, the subject has a mutation (i.e., a loss of function mutation) in the Dnase1l3 gene or the Dnase1 gene. In some embodiments, such subjects manifest with an autoimmune disease. In some cases, the subject has an acquired inhibitor of D1 and/or of D1L3. Such subjects can also have an autoimmune or inflammatory disease, such as SLE or systemic sclerosis.

In some embodiments, the subject has a loss of function mutation in one or both D1L3 genes, and may exhibit symptoms of SLE, or may be further diagnosed with clinical SLE. In such embodiments, the subject may receive systemic therapy with a BD-deleted D1L3 described herein. For example, therapeutically effective amounts of the fusion protein represented by SEQ ID NO:47, or other fusion between albumin and a BD-deleted D1L3, are administered once or twice weekly, or once or twice monthly.

Other aspects and embodiments of the invention will be apparent from the following examples.

BRIEF DESCRIPTION OF FIGURES

FIG. 3 shows 14 of the 63 D1L3-D1 chimeras (#50-#63), SEQ ID NOs: 8-21, respectively, generated using the building block substitution method.

FIG. 4 shows the chromatin-degrading activities of D1L3-D1 chimeras (#50 to #63) shown in FIG. 3. As shown, the D1L3-D1 chimera #63, which harbors a Q282_S305delinsK mutation (involving deletion of C-terminal basic domain (BD) and substitution of Glutamine 282 of D1L3 with a Lysine) (SEQ ID NO: 21), exhibits hyperactivity for chromatin degradation as compared to wild-type D1L3.

FIG. 5A shows a western blot of culture supernatants using a monoclonal antibody that targets MGDFNAGCSYV (SEQ ID NO:42) (Anti-D1/D1L3), a peptide sequence that is shared by D1 and D1L3. Mobility shift confirms the C-terminal deletion in the Q282_S305delinsK mutant. FIG. 5B shows the results of a titration experiment performed to compare the chromatin-degrading activities of wild type D1L3 and the BD-deleted D1L3. The results demonstrate that the BD-deleted D1L3 had approximately 5 to 10-fold higher enzymatic activity on HMW-chromatin compared to wild type D1L3.

FIG. 6 shows sequence alignment of C-termini of the S305del, K303_S305del, V294_S305del, K291_S305del, R285_S305del, and S283_S305del deletion mutants (SEQ ID NOs: 22-27, respectively), which lack 1, 3, 12, 15, 21, and 23 C-terminal amino acids, respectively.

FIG. 9A shows the ability to degrade ultra-large chromatin into mononucleosomes by the indicated deletion mutant enzymes in comparison with the wild type D1L3.

FIG. 11 shows that the addition of dextran sulfate to CHO medium improves protein yield. Stable pools of CHO cells expressing wild-type D1L3 were incubated in standard CHO medium or CHO medium supplemented with dextran sulfate. Supernatants were analyzed by Western Blot (WB) using an anti-DNASE1L3 antibody. The figure shows that D1L3 expresses poorly in CHO cells with low yield. Addition of dextran sulfate increases the yield, but does not prevent production fragmentation.

FIGS. 12A-B show that D1L3 has a propensity to misfold when expressed in CHO cells. FIG. 12A illustrates a simple expression vector for D1L3 expression using the native secretory signal peptide. Supernatants of stable pools were analyzed by Western Blot using an anti-DNASE1L3 antibody, and FIG. 12B shows the presence of high molecular weight aggregates under non-reducing conditions, which are resolved under reducing conditions.

FIG. 14 shows the location of NLS2 sequence superimposed with a sequence alignment of C-termini of the S305del, K303_S305del, V294_S305del, K291_S305del, R285_S305del, and S283_S305del deletion mutants, which lack 1, 3, 12, 15, 21, and 23 C-terminal amino acids, respectively.

DETAILED DESCRIPTION OF THE INVENTION

Figure 1:
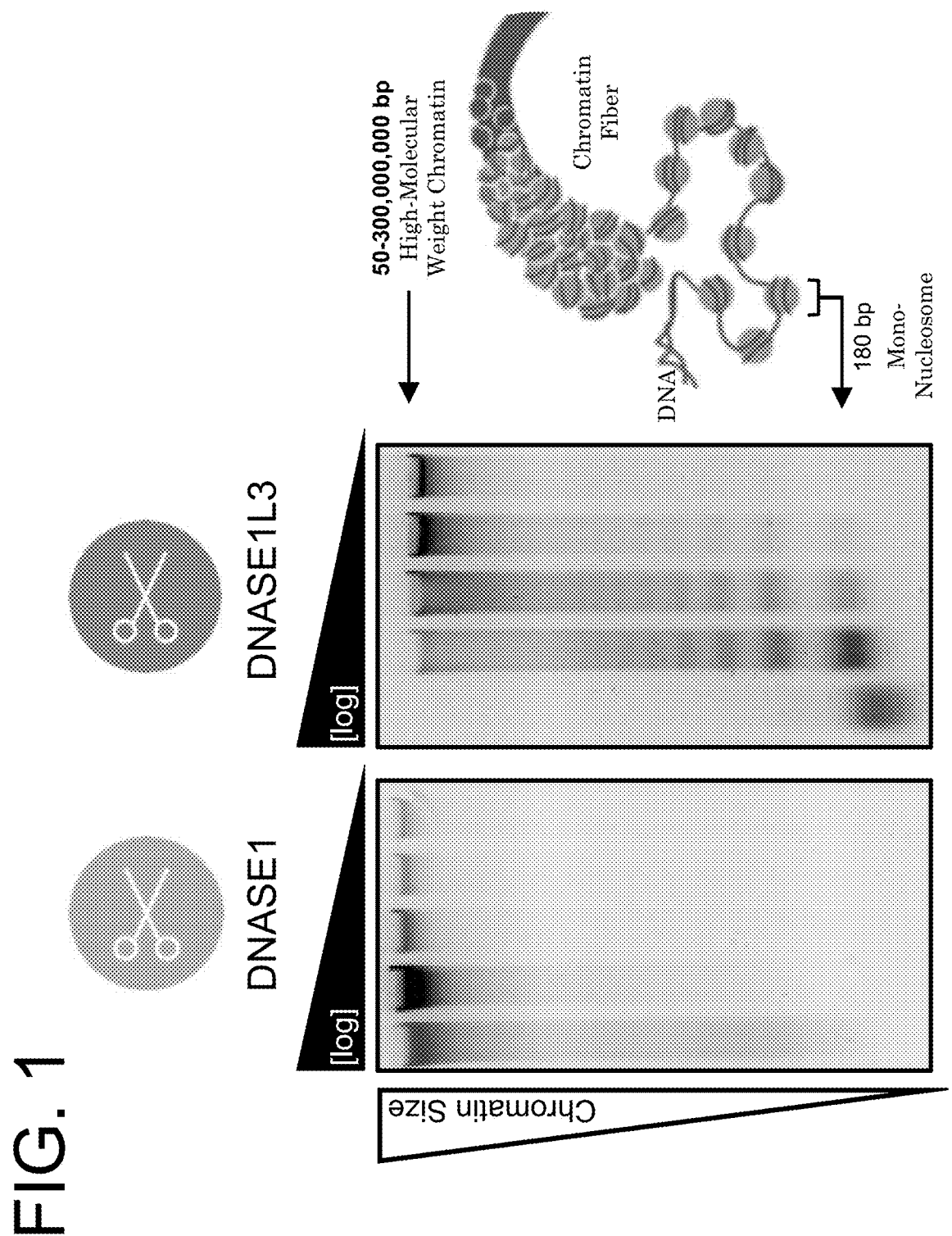
FIG. 1 shows the enzymatic activity of increasing amounts of DNASE1 (D1) and DNASE1-LIKE 3 (D1L3) as characterized by the degradation of high-molecular weight (HMW)-chromatin from HEK293 cell purified nuclei. D1 has limited activity for degrading chromatin as compared to D1L3.

The present disclosure is based, in part, on the discovery that D1L3 enzymes having complete or partial C-terminal deletions of the basic domain (BD) have substantially enhanced chromatin-degrading activity. In accordance with aspects of the invention, the D1L3 enzymes described herein are more suitable and/or effective for therapy and/or are more amenable to large-scale manufacturing. In some embodiments, the enzymes disclosed herein have benefits for systemic therapy, including cell therapy in which a host cell expresses a heterologous chromatinase such as D1L3. Such benefits include longer exposure (e.g., slower elimination, longer circulatory half-life), extended duration of pharmacodynamic action, and improved chromatin-degrading activity.

In the description that follows, certain conventions will be followed regarding the usage of terminology. As used herein and in the claims, the singular forms "a," "an," and "the" include the singular and the plural reference unless the context clearly indicates otherwise.

The term "chromatinase" refers to a class of deoxyribonuclease enzyme that exhibits more than a negligible ability to cut, cleave or digest chromatin, i.e., DNA associated with one or more histone proteins. Human DNASE1L3 is a chromatinase. DNASE1L3 variants disclosed herein are chromatinases. Not all DNASE enzymes are chromatinases. For example, human DNASE1 has essentially no ability to specifically cut, cleave, or digest chromatin and is not a chromatinase.

As used herein, unless stated to the contrary, the term "D1L3" when referring to the wild-type sequence, includes either D1L3 Isoform 1 (SEQ ID NO:4) or D1L3 Isoform 2 (SEQ ID NO:5).

When referring to sequence identity with wild-type DNase enzymes, and unless stated otherwise, sequences refer to mature enzymes lacking the signal peptide. Further, unless stated otherwise, amino acid positions are numbered with respect to the full-translated DNase sequence, including signal peptide, for clarity. Accordingly, for example, reference to sequence identity to the enzyme of SEQ ID NO: 4 (human D1L3, Isoform 1) refers to a percent identity with the mature enzyme having M21 at the N-terminus. Polynucleotides encoding enzymes may also encode the signal peptide to effect secretion from host cells and processing of the signal peptide.

As used herein with reference to a drug, "half-life" refers to the elimination half-life of the concentration of the drug in an animal, as measured in a matrix of interest, e.g., serum or plasma. The skilled person will understand that not all drugs exhibit first-order kinetics or do so during all phases of elimination. In such cases, the skilled person will understand that the terms "half-life extension" or "extended half-life" are expressions that refer to a slower rate of elimination.

As used herein, "neutrophil extracellular trap" and the acronym "NET" refer to a network of extracellular fibers comprising nuclear contents, e.g., DNA bound to histone proteins that are released from an immune cell, typically a neutrophil, in a programmed fashion.

Unless otherwise specified, a "nucleotide sequence" or "nucleic acid" encoding an amino acid sequence includes all degenerate versions that encode the same amino acid sequence. The phrase nucleotide sequence that encodes a protein or an RNA may also include introns to the extent that the nucleotide sequence encoding the protein may in some version contain one or more introns. In some embodiments, a polynucleotide encoding a chromatinase does not have introns.

The terms "about" and "approximately" include an amount that is 10% of an associated numerical value.

D1L3 features a 23-amino acid long C-terminal tail, which contains 9 basic amino acids and is thus known as Basic Domain (BD). The BD is unique to D1L3 and is not present in D1. The BD contains a nuclear localization signal (NLS) that targets the enzyme to the nucleus during apoptosis. While it has been widely considered that the BD is critical for the biologic activity of D1L3 in the extracellular space, this disclosure surprisingly shows that deletion of the C-terminal tail in fact stimulates chromatinase activity of D1L3.

In various embodiments, the invention provides a DNASE1-LIKE 3 (D1L3) enzyme comprising an amino acid sequence that has at least 70% sequence identity to D1L3 Isoform 1 (SEQ ID NO:4) or D1L3 Isoform 2 (SEQ ID NO:5) lacking the BD (i.e., at least 70% sequence identity with amino acids 21 to 282 of SEQ ID NO: 4, or amino acids 21 to 252 of SEQ ID NO:5), and wherein the D1L3 enzyme has a deletion of at least three amino acids from the BD. Amino acid deletions of the Basic Domain of D1L3 improve its chromatin-degrading activity. Further, increasing deletions of the 23-amino acid BD directly correlate with increasing chromatin-degrading activity, including activity for degrading mono-nucleosomes.

In various embodiments, the amino acid deletions from the BD are at the C-terminus of the BD. For example, the D1L3 enzyme may have a deletion of at least the five C-terminal amino acids of BD. In some embodiments, the D1L3 enzyme has a deletion of at least the eight C-terminal amino acids of the BD. In some embodiments, the D1L3 enzyme has a deletion of at least the ten C-terminal amino acids of the BD. In some embodiments, the D1L3 enzyme has a deletion of at least the twelve C-terminal amino acids of the BD. In some embodiments, the D1L3 enzyme has a deletion of at least the fifteen C-terminal amino acids of the BD. In some embodiments, the D1L3 enzyme has a deletion of at least the eighteen C-terminal amino acids of the BD. In some embodiments, the D1L3 enzyme has a deletion of at least the twenty one C-terminal amino acids of the BD. In some embodiments, the D1L3 enzyme has a deletion of at least the twenty three C-terminal amino acids of the BD.

Alternatively, deletions of the BD (from three to 23 amino acids) can be anywhere in the BD, and not necessarily from the C-terminus of the BD. For example, in various embodiments, the D1L3 enzyme has 3, 4, 5, 6, 7, 8, 9, 10, 11, 12, 13, 14, 15, 16, 17, 18, 19, 20, 21, 22, or 23 amino acids deleted from the BD. In some embodiments, the D1L3 enzyme has a deletion of at least 5, or at least 8, or at least 12, or at least 15, or at least 18, or at least 21 amino acids from the BD. These deletions can be independently selected from the N-terminal side of the BD, from the C-terminal side of the BD, and internal to the BD. In some embodiments, one or more amino acid deletions are within the NLS within the BD.

In addition to deletions of one or more amino acids, the BD may further comprise amino acid substitutions, which may further impact chromatin-degrading activity. For example, the D1L3 enzyme may have from 1 to 20 amino acid substitutions of BD amino acids, in addition to a deletion of at least three amino acids. In some embodiments, the BD contains a substitution of at least three amino acids, or at least five amino acids, or at least 10 amino acids. In some embodiments, at least two amino acid substitutions are in the NLS of the BD.

In some embodiments, the D1L3 enzyme has a deletion of one or more additional amino acids from the C-terminus, in addition to a deletion of the BD. For example, the D1L3 enzyme may have a deletion of an additional one to fifty amino acids, or from one to twenty amino acids, or from one to ten amino acids, or from one to five amino acids from the C-terminal amino acids of SEQ ID NO:4 or SEQ ID NO:5, in addition to the deletion of the BD.

In some embodiments, after partial or complete deletion of the BD as described, from 1 to 10 amino acids, or from 1 to 5 amino acids may be added to the C-terminus that do not impact chromatin-degrading activity.

In various embodiments, the D1L3 enzyme amino acid sequence has at least 80% sequence identity to the enzyme of SEQ ID NO: 4 and SEQ ID NO: 5 lacking the BD. In some embodiments, the D1L3 amino acid sequence has at least 85% sequence identity to the enzyme of SEQ ID NO: 4 and SEQ ID NO: 5 lacking the BD. In some embodiments, the D1L3 amino acid sequence has at least 90% sequence identity to the enzyme of SEQ ID NO: 4 and SEQ ID NO: 5 lacking the BD. In such embodiments, the amino acid sequence may have at least 95% sequence identity to the enzyme of SEQ ID NO: 4 and SEQ ID NO: 5 lacking the BD, or at least 97% sequence identity to the enzyme of SEQ ID NO: 4 and SEQ ID NO: 5 lacking the BD. In some embodiments, the D1L3 amino acid sequence has 100% sequence identity with the enzyme of SEQ ID NO:4 or SEQ ID NO:5 lacking the BD.

In still other aspects, the invention provides a DNASE-LIKE 3 (D1L3) enzyme comprising an amino acid sequence that has at least 70% sequence identity to D1L3 Isoform 1 (SEQ ID NO:4) or D1L3 Isoform 2 (SEQ ID NO:5), and wherein the D1L3 enzyme has a single amino acid truncation of the BD. D1L3 enzymes having a single amino acid truncation from the BD have surprisingly high DNase activity.

In some embodiments, the D1L3 enzyme comprises additional modifications outside the BD, and which can provide additional advantages, including advantages in stability and compatibility with expression systems. Such modifications are disclosed in US 2020/0024585, PCT/US2019/055178, or PCT/US2020/016490, each of which are hereby incorporated by reference in its entirety.

In some embodiments, the D1L3 enzyme comprises at least one building block substitution from D1 (SEQ ID NO:1), DNASE-1-LIKE 1 (D1L1) (SEQ ID NO:2), or DNASE-1-LIKE 2 (SEQ ID NO:3). These building block substitutions are disclosed in PCT/US2020/016490, which is hereby incorporated by reference in its entirety.

In some embodiments, the D1L3 sequence or domain contains a building block substitution from D1 defined by amino acid sequences, which can be selected from: M1_A20delinsMRGMKLLGALLALAALLQGAVS, M21_S25delinsLKIAA, V28_S30delinsIQT, E33_S34delinsET, Q36_I45delinsMSNATLVSYI, K47_K50delinsQILS, C52Y, I54_M58delinsIALVQ, I60_K61delinsVR, S63_I70delinsSHLTAVGK, M72_K74delinsLDN, R77_T84delinsQDAPDT, N86H, V88_I89delinsVV, S91_R92delinsEP, N96_T97delinsNS, Q101R, A103L, L105V, K107_L110delinsRPDQ, V113_S116delinsAVDS, H118Y, H120D, Y122_AI27delinsGCEPCGN, V129T, S131N, 135F_136VdelinsAI, W138R, Q140_H43delinsFSRF, A145_D148delinsAVKD, V150A, I152A, T156_TI57delinsAA, E159_SI61delinsGDA, K163A, E167A, V169_E70delinsYD, T173L, K176_R178delinsQEK, K180_AI81delinsGL, N183_FI86delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259_A260delinsAA, K262G, T264_E267delinsSDQL, L269_V271delinsQAI, F275Y, F279_K280delinsVM, and Q282_S305delinsK.

In some embodiments, the D1L3 enzyme is fused to a carrier protein, optionally by means of an amino acid linker. The carrier protein is generally a half-life extending moiety, such as albumin, transferrin, an Fc, XTEN, or elastin-like protein, or a variant thereof. See, e.g., U.S. Pat. No. 9,458,218, which is hereby incorporated by reference in its entirety.

In some embodiments, the D1L3 enzyme is fused to an albumin amino acid sequence or domain, i.e., a human albumin or a fragment or variant thereof. See, for example, WO 2015/066550 and U.S. Pat. No. 9,221,896, which are hereby incorporated by reference in their entirety. Albumin can be joined to the D1L3, optionally with an interposed linker, at the N-terminus and/or the C-terminus of the D1L3 enzyme. An exemplary albumin amino acid sequence is provided by SEQ ID NO: 39. In some embodiments, the D1L3 enzyme comprises an albumin sequence fused to the N-terminus of the mature D1L3 enzyme with an interposed amino acid linker.

In some embodiments, the albumin amino acid sequence or domain of the fusion protein has at least about 75%, or at least about 80%, or at least about 85%, at least 90%, at least 95%, at least 97%, at least 98%, or at least 99% sequence identity to the reference albumin sequence defined by SEQ ID NO: 39. In some embodiments, the albumin amino acid sequence or domain comprises or consists of the reference albumin sequence defined by SEQ ID NO: 39. In various embodiments, the albumin amino acid sequence binds to the neonatal Fc receptor (FcRn), e.g., human FcRn. The albumin amino acid sequence may be a variant of wild-type HSA (e.g., as represented by SEQ ID NO: 39). In various embodiments, albumin variants may have from one to twenty, or from one to ten amino acid modifications independently selected from deletions, substitutions, and insertions with respect to SEQ ID NO: 39. In some embodiments, the albumin amino acid sequence is any mammalian albumin amino acid sequence. Various modification to the albumin sequence that enhance its ability to serve as a circulation half-life extending carrier are known, and such modifications can be employed with the present invention. Exemplary modifications to the albumin amino acid sequence are described in U.S. Pat. Nos. 8,748,380, 10,233,228, and 10,501,524, which are each hereby incorporated by reference in their entireties.

In some embodiments, the albumin amino acid sequence or domain is a fragment of full-length albumin, as represented by SEQ ID NO: 39. The term "fragment," when used in the context of albumin, refers to any fragment of full-length albumin or a variant thereof (as described above) that extends the half-life of a D1L3 enzyme to which it is fused or conjugated, relative to the corresponding non-fused D1L3. In some embodiments, a fragment of an albumin can refer to an amino acid sequence comprising a fusion of multiple domains of albumin (see, e.g., WO2011/124718), such as domains I and III, and domains II and III. Generally, a fragment of albumin has at least about 100 amino acids or at least about 200 or at least about 300 amino acids of the full-length sequence. In various embodiments, the albumin fragment maintains the ability to bind human FcRn.

In some embodiments, the D1L3 enzyme is fused at the N-terminus to an albumin amino acid sequence, through a peptide linker. The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length. In some embodiments, the linker is from about 10 to about 35 amino acids in length, or from about 15 to about 35 amino acids.

Flexible linkers are predominately or entirely composed of small, non-polar or polar residues such as Gly, Ser and Thr. An exemplary flexible linker comprises $(Gly_y Ser)_n S_z$ linkers, where y is from 1 to 10 (e.g., from 1 to 5), n is from 1 to about 10, and z is 0 or 1. In some embodiments, n is from 3 to about 8, or from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is $A(EAAAK)_n A$, where n is as defined above (e.g., from 1 to 10, or 3 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 31 to 38.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise or consist of S(GGS)$_4$GSS (SEQ ID NO: 36), S(GGS)$_9$GSS (SEQ ID NO: 37), (GGS)$_9$GSS (SEQ ID NO: 38). In some embodiments, the linker has at least 10 amino acids, or at least 15 amino acids, or at least 20 amino acids, or at least 25 amino acids, or at least 30 amino acids. For example, the linker may have a length of from 15 to 40 amino acids. In various embodiments, longer linkers of at least 15 amino acids can provide improvements in yield upon expression in *Pichia pastoris*. See PCT/US2019/055178, which is hereby incorporated by reference in its entirety.

An exemplary fusion protein for use in systemic therapy is shown as SEQ ID NO: 47, which includes an N-terminal albumin amino acid sequence, a flexible linker of 31 amino acids, and a mature D1L3 amino acid sequence having a full deletion of the BD.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 40) and/or prekallikrein (SEQ ID NO: 41) or a physiologically cleavable fragment thereof. In selected embodiments, the linker amino acid sequence from Factor XI contains all or parts of SEQ ID NO: 40 (e.g., parts of SEQ ID NO: 40, including modifications of SEQ ID NO: 40 that allow for cleavage by Factor XIIa). In some embodiments, the linker amino acid sequence from prekallikrein contains all or parts of SEQ ID NO: 41 (e.g., parts of SEQ ID NO: 41, including modifications of SEQ ID NO: 41 that allow for cleavage by Factor XIIa). In other embodiments, the linker includes a peptide sequence that is targeted for cleavage by a neutrophil specific protease, such as neutrophil elastase, cathepsin G, and proteinase 3.

The chromatin- and/or NET-degrading activity of a D1L3 enzyme variant, e.g., comprising a deletion of one or more amino acids of the BD, can be measured in vitro, for example by incubation of the enzyme with chromatin or NETs. Chromatin or NETs can be obtained in some embodiments from purified nuclei or ex vivo blood or neutrophils induced to form NETs. Alternatively, the chromatin- and/or NET-degrading activity of an enzyme can be measured in vivo, for example by administering the enzyme to a subject, wherein the subject produces or is induced to produce extracellular DNA, chromatin or NETs, and measuring the effect of the enzyme on concentrations of DNA, chromatin, or NET levels in a matrix, e.g. serum, preferably with a parallel negative control, or by temporally comparing the concentrations before and after administration of the enzyme.

In some embodiments, the fusion protein is synthesized with a signal peptide. The signal peptide may be removed during secretion from the host cell. With respect to expression in *Pichia pastoris*, the alpha-mating factor (uMF) pre-pro secretion leader from *Saccharomyces cerevisiae* (SEQ ID NO: 28) may be used for expression. In other embodiments, the signal peptide and propeptide of HSA, which consists of a signal sequence of 24 amino acids (MKWVTFISLLFLFSSAYSRGVFRR; SEQ ID NO: 29) may be used. In some embodiments, the human DNASE1L3 Signal Peptide (Q13609) (SEQ ID NO: 30) is used for expression. These elements are cleaved during expression, and are not present in the D1L3 enzyme product.

The invention in some aspects provides pharmaceutical compositions comprising the D1L3 enzyme described herein, or optionally a polynucleotide encoding the D1L3 enzyme, or a transfection or expression vector comprising the same, and a pharmaceutically acceptable carrier.

In some embodiments, delivery of polynucleotides is used for therapy. Encoding polynucleotides can be delivered as mRNA or as DNA constructs using known procedures, e.g., electroporation or cell squeezing, and/or vectors (including viral vectors). mRNA polynucleotides can include known modifications (mmRNA) to avoid activation of the innate immune system. See WO 2014/028429, which is hereby incorporated by reference in its entirety. In some embodiments, the polynucleotide is delivered to the body of a subject.

In some embodiments, the polynucleotide is delivered into a cell in vitro, and the cell is delivered to the body of a subject. The cell can be, for example, a white blood cell (e.g., a T cell or macrophage), an endothelial cell, an epithelial cell, a hepatocyte, or a stem cell (e.g., LT-HSC). In these aspects, the invention provides mammalian host cells (e.g., human host cells) (as well as methods of making and using the same) that comprise a heterologous polynucleotide encoding a chromatinase enzyme operably linked to a promoter. The host cell expresses and secretes the chromatinase enzyme. In these aspects, challenges in manufacturing chromatinases such as D1L3 at large scale are avoided. Further, by expressing and delivering D1L3 through heterologous expression in a white blood cell such as a T cell, D1L3 therapy can be localized in part to areas of inflammation or tissue destruction or cell apoptosis. Further, since D1L3 has a circulation half-life of less than about 30 minutes, the cell therapy described herein provides for a sustained therapy, with as few as one, two, three, or four treatments. In various embodiments, a subject can be treated with ten or fewer administrations of the cellular therapy, or with four or fewer treatments of the cellular therapy. While T cells (and other host cells) can be engineered to express D1L3 having whole or partial deletions of the C-terminal BD (as described herein), because T cells express PCSK types 3, 5, 6, and 7 (including Furin, PCSK3), expression of wild type D1L3 can be activated by T cells through cleavage within the C-terminal BD. Exemplary T cells include CD4+ T cells or CD8+ T cells (e.g., CTLs). In some embodiments, the T cell is a regulatory T cell ($T_{reg}$). T cells such as gamma delta T cells or Chimeric Antigen Receptor (CAR)-T cells can be employed in certain embodiments. In some embodiments, the CAR-T cells are directed against CD19. In some embodiments, D1L3 C-terminal basic domain processing is induced when the T cell is activated (e.g., by activation of the TCR or CAR). Exemplary T cells can comprise memory T cells, such as (in order of proliferative capacity) T memory stem cells, central memory T cells, or effector memory T cells. In some embodiments, the T cells are predominately terminally differentiated T cells.

Exemplary T cells for chromatinase cell therapy may recognize (through the TCR or CAR) a cancer-associated antigen, such as a leukemia-associated antigen, or an antigen of a solid tumor. In some embodiments, the T cell recognizes a viral antigen, including but not limited to an oncovirus. Exemplary oncoviruses include Epstein-Barr virus, human papilloma virus, hepatitis B or C virus, human herpes virus (e.g., HSV8), and human T lymphotrophic virus. In some embodiments, the T cell recognizes a coronavirus antigen, such as SARS-CoV-2.

In some embodiments, the host cell (e.g., a T cell) secretes D1L3 enzyme having a deletion of at least 12 amino acids of the C-terminal BD. In some embodiments, the secreted D1L3 enzyme includes enzymes having deletions of one or more of: K291_S305 del, K292_S305 del, K293_S305 del, with respect to SEQ ID NO:4. In these or other embodiments, the polynucleotide encodes a D1L3 enzyme having a deletion of one or more amino acids of the C-terminal BD, such as at least three or at least five amino acids of the C-terminal BD. In some embodiments, the polynucleotide encodes a D1L3 enzyme having a deletion of at least 12 amino acids of the BD, or a complete deletion of the BD.

In some embodiments, the polynucleotide encodes a D1L3 enzyme having an inactivation or mutation of one or more of the NLS1 and the NLS2. D1L3 features two nuclear localization sites (NLS1, NLS2), which may target the enzyme to the nucleus during apoptosis. NLS1 is located near the N-terminus (about amino acid positions 80 to 96 with respect to SEQ ID NO:4). NLS2 (amino acid positions 291 to 304 with respect to SEQ ID NO:4) is embedded within the C-terminal BD. In some embodiments, the NLS inactivation is by deletion of all or part of NLS1 and/or NLS2. In some embodiments, the NLS is inactivated by substitution and/or deletion of amino acids within NLS1 and/or NLS2. In some embodiments, NLS2 is deleted, entirely or partially.

In certain embodiments, the D1L3 enzyme contains one or more, e.g., 1, 2, 3, 4, 5, or more amino acid substitutions, additions (e.g., insertions), or deletions in the NLS1. In certain embodiments, the D1L3 enzyme contains one or more, e.g., 1, 2, 3, 4, 5, or more amino acid substitutions, additions, or deletions in the NLS2.

In these or other embodiments, the polynucleotide may express the D1L3 fused to a carrier protein as described (e.g., albumin), which is optionally linked at the N-terminus of D1L3 enzyme through a flexible or cleavable linker (as described).

A vector generally comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Exemplary vectors include autonomously replicating plasmids or a virus (e.g. AAV vectors). The term should also be construed to include non-plasmid and non-viral compounds that facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

In some embodiments, the polynucleotide or cell therapy may employ expression vectors, which comprise the nucleic acid encoding the chromatinase (e.g., D1L3) operably linked to an expression control region that is functional in the host cell. The expression control region is capable of driving expression of the operably linked encoding nucleic acid such that the chromatinase is produced in a human cell transformed with the expression vector. Expression control regions are regulatory polynucleotides (sometimes referred to herein as elements), such as promoters and enhancers, that influence expression of an operably linked nucleic acid. An expression control region of an expression vector is capable of expressing operably linked encoding nucleic acid in a human cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. In various embodiments, the chromatinase expression is inducible or repressible. Typically, the amount of increase or decrease conferred by such elements is proportional to the amount of signal present; the greater the amount of signal, the greater the increase or decrease in expression.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription-initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), FIp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family, and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences including CRISPR/CAS9, zinc finger, transcription activator-like effector nuclease (TALEN), and meganuclease gene-editing technologies.

The pharmaceutical composition may be formulated for any administration route, including topical, parenteral, or pulmonary administration. In various embodiments, the composition is formulated for intravenous, intradermal, intramuscular, intraperitoneal, intraarticular, subcutaneous, or intraarterial. In some embodiments, the composition is formulated for intravenous or subcutaneous administration. In some embodiments, the composition comprises an effective amount of host cells (expressing a chromatinase such as D1L3) for delivery (e.g., by infusion). An effective amount of host cells to be delivered by the composition can be determined by one of skill in art, and may include, for example, at least about $10^6$ cells, at least about $10^7$ cells, at least about $10^8$ cells, or at least about $10^9$ cells.

In other aspects, the present technology provides a method for treating a subject in need of extracellular chromatin degradation, extracellular trap (ET) degradation and/or neutrophil extracellular trap (NET) degradation. The method comprises administering a therapeutically effective amount of the D1L3 enzyme or composition described herein. Exemplary indications where a subject is in need of extracellular chromatin degradation (including ET or NET degradation) are disclosed in PCT/US18/47084, the disclosure of which is hereby incorporated by reference. In some embodiments, the method comprising administering the isolated host cells described herein (expressing a chromatinase for secretion) to the subject. In some embodiments, the subject is at risk of occlusions involving extracellular chromatin, including chromatin released by cancer cells and injured endothelial cells, among others. Thus, in exemplary embodiments, the subject has cancer (e.g., leukemia or solid tumor). In some embodiments, the subject has metastatic cancer.

Subjects receiving therapy for cancer (including but not limited to T cell therapies) are at risk of tumor lysis syndrome, which occurs when tumor cells release their contents (including chromatin) into the bloodstream. Tumor lysis syndrome is a complication during the treatment of cancer, where large amounts of tumor cells are killed at the same time. Tumor lysis syndrome occurs commonly after the treatment of lymphomas and leukemias.

In still other embodiments, the subject has an inflammatory disease of the respiratory tract, such as the lower respiratory tract. Exemplary diseases include bacterial and viral infections. In some embodiments, the subject has Acute Respiratory Distress Syndrome (ARDS), Acute Lung Injury (ALI), or pneumonia. Exemplary viral infections include RSV and coronavirus infection (such as SARS, or SARS-CoV-2, e.g., COVID-19 as well as variants thereof).

Neutrophils, the predominant leukocytes in acute inflammation, generate neutrophil extracellular traps (NETs), lattices of high-molecular weight chromatin filaments decorated with biologically active proteins and peptides, which immobilize bacteria in wounds. Systemic accumulation of NETs harms tissues and organs due to their cytotoxic, proinflammatory, and prothrombotic activity. Indeed, NETs are frequently associated with inflammatory, ischemic, and autoimmune conditions, including Systemic Lupus Erythematosus (SLE).

In various embodiments, the present invention provides a method for treating, preventing, or managing diseases or conditions characterized by the presence or accumulation of NETs. Such diseases or conditions include, but are not limited to, diseases associated with chronic neutrophilia, neutrophil aggregation and leukostasis, thrombosis and vascular occlusion, ischemia-reperfusion injury, surgical and traumatic tissue injury, an acute or chronic inflammatory reaction or disease, an autoimmune disease, cardiovascular disease, metabolic disease, systemic inflammation, inflammatory diseases of the respiratory tract, renal inflammatory diseases, inflammatory diseases related to transplanted tissue (e.g. graft-versus-host disease) and cancer (including leukemia).

In some embodiments, the subject has SLE. The discovery of NETs raised the speculation that neutrophils may be the predominant source of autoantigens (i.e. dsDNA, chromatin) in SLE (Brinkmann, et al. *Neutrophil Extracellular Traps Kill Bacteria.* Science, 303(5663): 1532-1545 (2004). Indeed, autoantibodies such as anti-dsDNA, -histone, and -nucleosome antibodies bind to NETs, forming pathological ICs. Hakkim, et al., *Impairment of neutrophil extracellular trap degradation is associated with lupus nephritis, Proceedings of the National Academy of Sciences* 107: 9813-9818 (2010). The accumulation of NET-IC breaks immune tolerance via activation of adaptive immune cells that lead to the production of autoantibodies against NET components, forming a vicious cycle of inflammation and autoimmunity. Gupta and Kaplan, *The role of neutrophils and NETosis in autoimmune and renal diseases. Nat Rev Nephrol.* 12(7): 402-13 (2016). Therefore, reducing accumulation of NETs can break the cycle and thus provide an attractive therapeutic strategy for SLE.

In certain embodiments, the present invention pertains to the treatment of diseases or conditions characterized by deficiency of D1L3, or a deficiency of D1. In some cases, the subject has a mutation (e.g., a loss of function mutation) in the Dnase1l3 gene or the Dnase1 gene. Such subjects can manifest with an autoimmune disease, such as: systemic lupus erythematosus (SLE), lupus nephritis, scleroderma or systemic sclerosis, rheumatoid arthritis, inflammatory bowel disease, Crohn's disease, ulcerative colitis, and urticarial vasculitis. In some cases, the subject has an acquired inhibitor of D1 (e.g., anti-DNase1-antibody and actin) and/or D1L3 (e.g., anti-Dnase1l3-antibody). Such subjects can also have an autoimmune or inflammatory disease (e.g., SLE, systemic sclerosis).

In some embodiments, the subject has or is at risk of NETs occluding ductal systems. For example, the D1L3 enzymes or compositions disclosed herein can be administered to a subject to treat pancreatitis, cholangitis, conjunctivitis, mastitis, dry eye disease, obstructions of vas deferens, or renal diseases.

In some embodiments, the subject has or is at risk of NETs accumulating on endothelial surfaces (e.g. surgical adhesions), the skin (e.g. wounds/scarring), or in synovial joints (e.g. gout and arthritis, e.g., rheumatoid arthritis). The D1L3 enzymes and compositions described herein can be administered to a subject to treat a condition characterized by an accumulation of NETs on an endothelial surface such as, but not limited to, a surgical adhesion.

Other diseases and conditions associated with NETs, which the D1L3 enzymes or compositions disclosed herein may be used to treat or prevent, include: ANCA-associated vasculitis, asthma, chronic obstructive pulmonary disease, a neutrophilic dermatosis, dermatomyositis, burns, cellulitis, meningitis, encephalitis, otitis media, pharyngitis, tonsillitis, pneumonia, endocarditis, cystitis, pyelonephritis, appendicitis, cholecystitis, pancreatitis, uveitis, keratitis, disseminated intravascular coagulation, acute kidney injury, acute respiratory distress syndrome, shock liver, hepatorenal syndrome, myocardial infarction, stroke, ischemic bowel, limb ischemia, testicular torsion, preeclampsia, eclampsia, and solid organ transplant (e.g., kidney, heart, liver, and/or lung transplant). Furthermore, the D1L3 enzymes or compositions disclosed herein can be used to prevent a scar or contracture, e.g., by local application to skin, in an individual at risk thereof, e.g., an individual with a surgical incision, laceration, or burn.

In various embodiments, the subject has a disease that is or has been treated with wild-type Dnases, including D1 and streptodornase. Such diseases or conditions include thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, alum-induced inflammation, hepatorenal injury, pleural exudations, hemothorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test, pneumococcal meningitis, gout, leg ulcers, cystic fibrosis, Kartegener's syndrome, asthma, lobar atelectasis, chronic bronchitis, bronchiectasis, lupus, primary ciliary dyskinesia, bronchiolitis, empyema, pleural infections, cancer, dry eyes disease, lower respiratory tract infections, chronic hematomas, Alzheimer's disease, and obstructive pulmonary disease.

In some embodiments, the subject has a loss of function mutation in one or both D1L3 genes, and may exhibit symptoms of SLE, or may be further diagnosed with clinical SLE. In such embodiments, the subject may receive systemic therapy with a BD-deleted D1L3 described herein, such as the fusion protein represented by SEQ ID NO:47. In various embodiments, therapeutically effective amounts of the fusion protein represented by SEQ ID NO:47, or other fusion between albumin and a BD-deleted D1L3, are administered once or twice weekly, or once or twice monthly.

Other aspects and embodiments of the invention will be apparent from the following examples.

EXAMPLES

Example 1: Creating Chimeric DNase Enzymes

In this Example, chimeric DNase enzymes were created to evaluate the potential to create novel DNase enzymes for therapy against disorders caused by the accumulation of extracellular chromatin, including NETs. To produce variants of D1L3, transient transfection of in vitro expression systems [e.g. Chinese hamster ovary (CHO) cells or HEK293 cells] was used. Enzymatic activity in culture supernatants was characterized using the degradation of high-molecular weight (HMW)-chromatin (i.e. purified nuclei from HEK293 cells) as a readout. In brief, HMW-chromatin was first incubated with the D1L3 variants, followed by DNA isolation and visualization via agarose gel electrophoresis (AGE). As shown in FIG. 1, it was observed that, unlike D1, D1L3 degrades HMW-chromatin (app. 50-300,000,000 base pairs) specifically and efficiently into nucleosomes (app. 180 base pairs), the basic units of chromatin fibers, whereas no such effect was observed in samples with D1.

Figure 2:
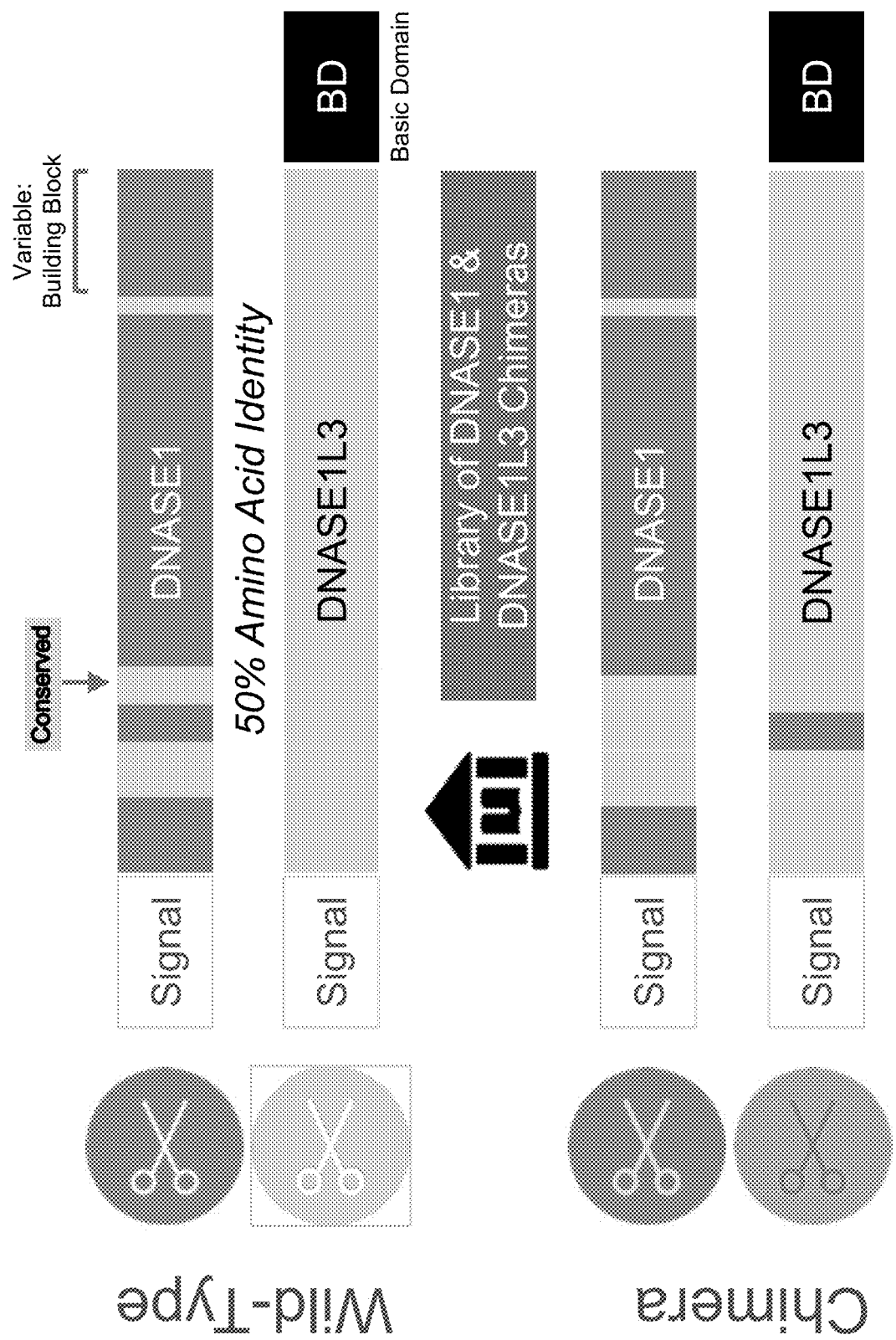
FIG. 2 shows a schematic representation of a building block substitution technology used for creating chimeric DNase enzymes. Summarily, building block substitution involves protein-protein sequence alignment of a donor DNase (e.g. DNASE1) and a recipient DNase (e.g. DNASE1L3), identification of variable amino acid blocks (building block) between conserved anchors, and substitution of a segment of cDNA encoding a building block from the recipient DNase with a segment of cDNA between the anchors in the donor DNase, thereby creating chimeric DNase enzymes.

We aimed to identify the regions of D1L3 that are responsible for its chromatin degrading activity. Sequence alignments of human D1 and human D1L3 were performed. The sequence alignments showed that 44% of the amino acids in human D1 and human D1L3 are identical. Without being bound by theory, it was speculated that the capacity of human D1L3 to degrade chromatin is mediated by amino acids that are not present in D1. Thus, only the variable amino acids (56% non-shared amino acids) were mutated to generate D1L3 variants. The method used to transfer enzymatic properties from D1 to D1L3 (building block-technology) is schematically represented in FIG. 2. The following cardinal steps characterize the building block substitution approach:

(1) Provide protein-protein alignment of donor (DNASE1) and recipient DNase (DNASE1L3);

(2) Identify variable amino acid or amino acid sequence for transfer (building block);

(3) Identify conserved amino acids in donor and recipient DNase that are located up and downstream of building blocks, respectively ("anchors"); (4) Replace the cDNA sequences encoding building block sequences, which are flanked by the C- and N-terminal anchors from a recipient DNase, with the cDNA sequence between the corresponding anchors from donor DNase;

(5) Synthesize a cDNA encoding the chimeric DNase. Prepare an expression vector capable of expressing the chimeric DNase, which harbors the cDNA of the chimeric DNase, operably linked to a promoter, terminator and/or other regulatory sequences of interest.

Chimeric DNase-encoding polynucleotides can be introduced and expressed into a recipient organism/cell of interest, which is preferably deficient in both donor and recipient DNase (e.g. CHO cells or Dnase1$^{-/-}$Dnase1l3$^{-/-}$ mice).

Example 2: Biochemical Characterization of the Chimeric Enzymes

Figure 3:
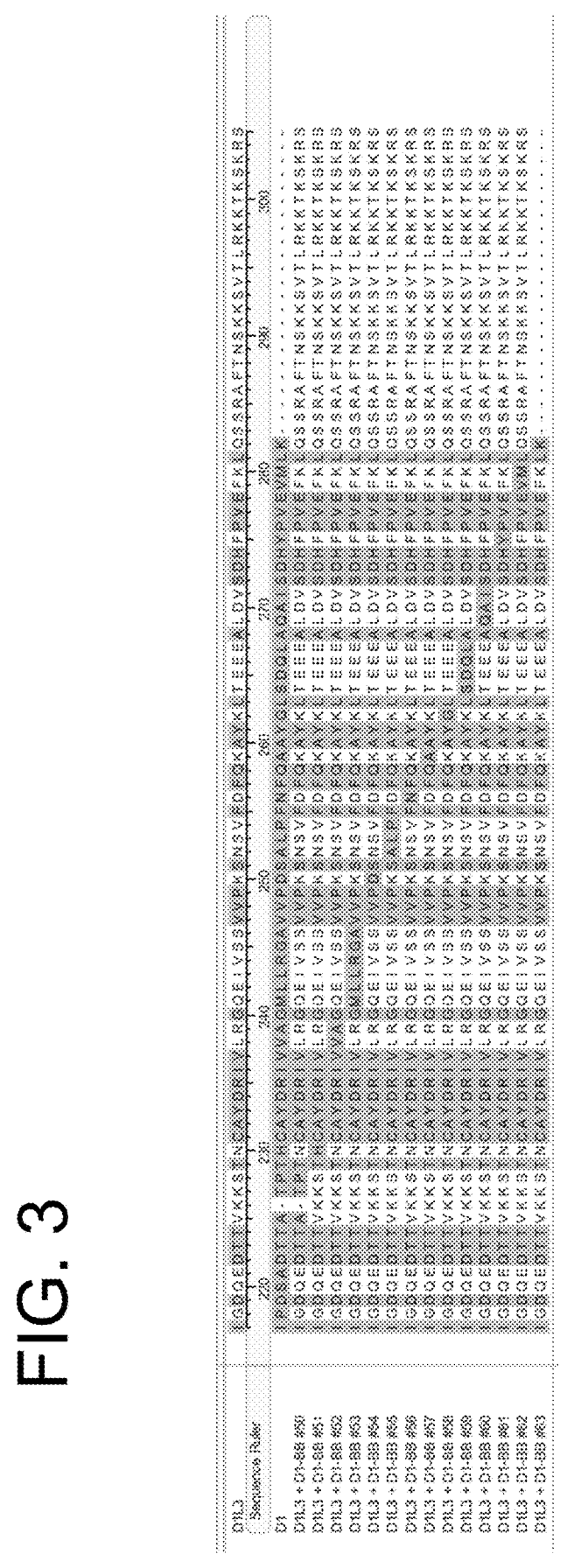

Using the building block substitution approach, 63 D1L3-D1 chimeras were generated (FIG. 3). These chimeras included D1L3-variants with the following building block mutations (BB): M1_A20delinsMRGMKLLGALLALAALLQGAVS, M21_S25delinsLKIAA, V28_S30delinsIQT, E33_S34delinsET, Q36_145delinsMSNATLVSYI, K47_K50delinsQILS, C52Y, 154_M58delinsIALVQ, 160_K61delinsVR, S63_I70delinsSHLTAVGK, M72_K74delinsLDN, R77_T84delinsQDAPDT, N86H, V88_I89delinsVV, S91_R92delinsEP, N96_T97delinsNS, Q101R, A103L, L105V, K107_L110delinsRPDQ, V113_S116delinsAVDS, H118Y, H120D, Y122_A127delinsGCEPCGN, V129T, S131N, 135F_136VdelinsAI, W138R, Q140_H143delinsFSRF, A145_D148delinsAVKD, V150A, I152A, T156_T157delinsAA, E159_S161delinsGDA, K163A, E167A, V169_E170delinsYD, T173L, K176_R178delinsQEK, K180_A181delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259_A260delinsAA, K262G, T264_E267delinsSDQL, L269_V271delinsQAI, F275Y, F279_K280delinsVM, and Q282_S305delinsK.

The D1L3-variants were transiently expressed in CHO cells and culture supernatants were screened for the activity to degrade high molecular weight (HMW)-chromatin. The reaction mixtures of HMW-chromatin degradation assay were examined by agarose gel electrophoresis (AGE) to assess the activity of the D1L3-D1 chimera. As shown in FIG. 4, these assays led to the identification of Q282_S305delinsK (i.e. BB #63), which confers hyperactivity on D1L3.

The mutation Q282_S305delinsK causes a complete deletion of the BD domain and the substitution of Q282 (glutamine at position 282) of D1L3 with a K (Lysine). As shown in FIG. 5A, the deletion of the C-terminal BD was confirmed using Western Blotting of culture supernatants using a monoclonal antibody that targets MGDFNAGCSYV (SEQ ID NO:42) (Anti-D1/D1L3), a peptide sequence that is shared by D1 and D1L3. The data further illustrated similar protein concentration of wild-type and mutated D1L3, indicating a lack of toxicity or altered protease sensitivity of the Q282_S305delinsK mutant D1L3 protein in the expression system (FIG. 5A).

Figure 5C:
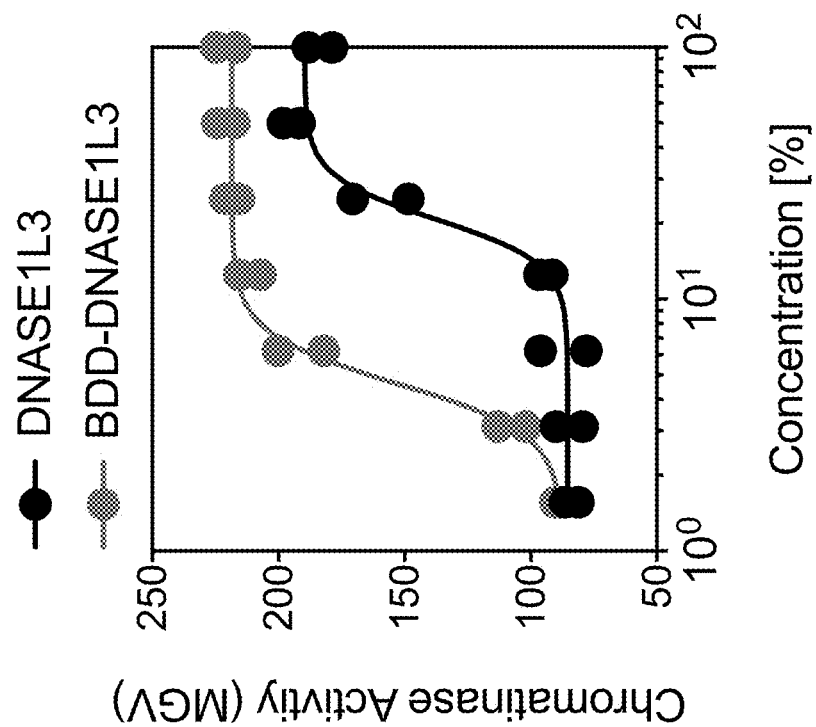
FIG. 5C is a graph showing chromatinase activity of wild type D1L3 and the BD-deleted D1L3 as a function of enzyme concentration.

To compare the enzymatic activity of wild type and Q282_S305delinsK mutant D1L3 proteins, a titration experiment was performed: high molecular weight chromatin was digested with increasing amounts of the enzymes, and reaction products were resolved by agarose gel electrophoresis (AGE). As shown in FIG. 5B, titration of culture supernatants showed that BD-deleted D1L3 had approximately 5- to 10-fold higher activity to degrade HMW-chromatin. The extent of chromatinase activity of wild type and Q282_S305delinsK mutant D1L3 proteins was calculated based on the quantitation of degraded chromatin (FIG. 5C). Collectively, the data suggest that the BD domain of D1L3 is not required for chromatin degradation, but rather suppresses enzymatic activity.

Example 3: Comparison of Different C-Terminal Truncation Mutants

Figure 7:
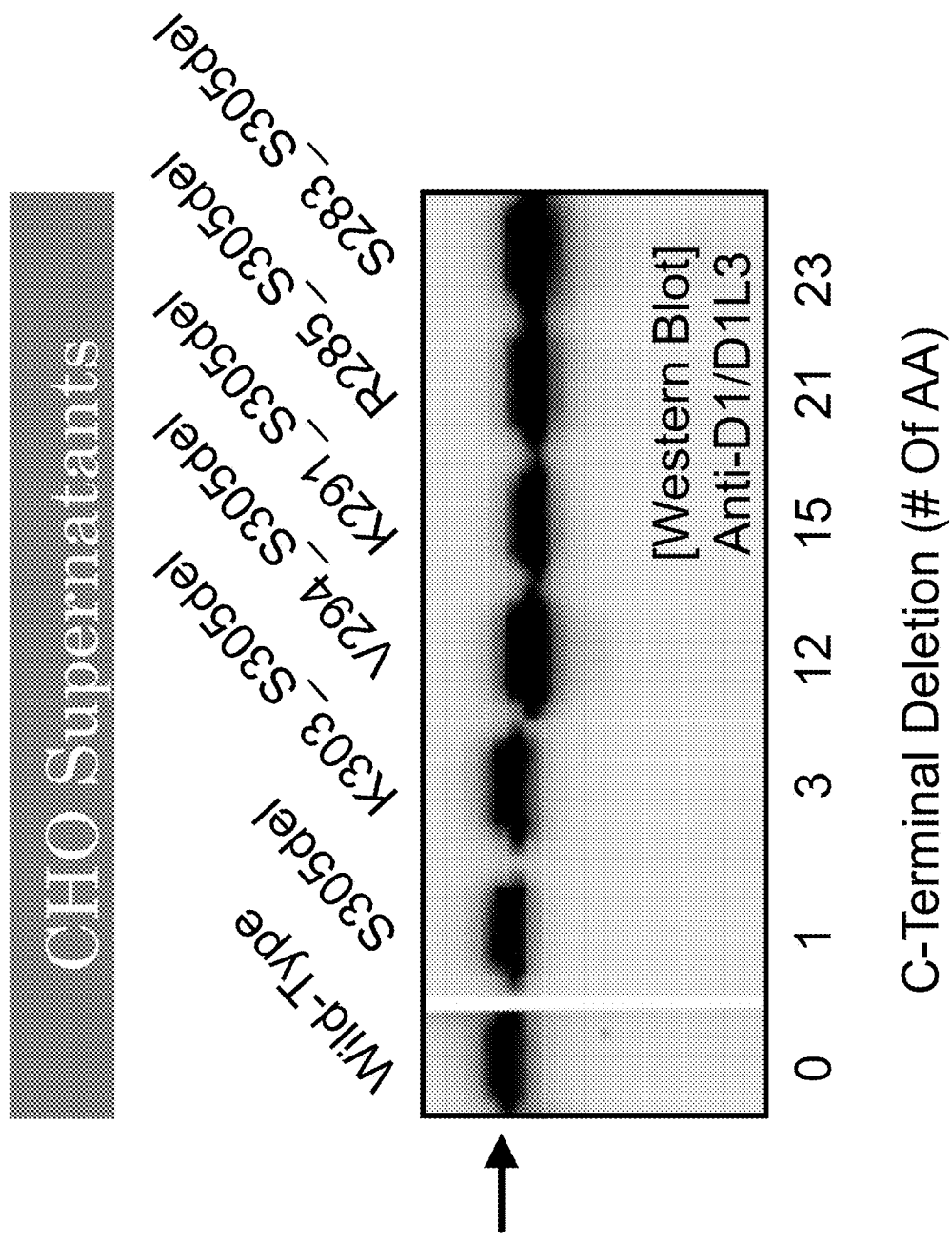
FIG. 7 shows a western blot of CHO cell culture supernatants after transient transfection of deletion mutants using the anti-D1/D1L3 antibody.

Since the Q282_S305delinsK mutation lacking the BD domain showed approximately 5- to 10-fold higher chromatinase activity compared to wild type D1L3 protein, the effect of extent of C-terminal deletion was evaluated. Whether full or partial truncation of BD of D1L3 is required to enable chromatin degradation was explored. Deletion mutants S305del, K303_S305del, V294_S305del, K291_S305del, R285_S305del, and S283_S305del, which lack 1, 3, 12, 15, 21, and 23 C-terminal amino acids, respectively were designed (FIG. 6). CHO and HEK293 cells were transiently transfected with vectors expressing wild-type and truncation mutants. Culture supernatants containing DTL3 and the variants were collected and tested by Western Blot using the aforementioned anti-D1/D1L3 antibody. As shown in FIG. 7, wild-type D1L3 as well as variants of smaller molecular weight could be detected. The observed mobility shift, inter alia, confirmed the deletion of BD. Furthermore, the western blots showed that all C-terminal truncation mutants and the wild-type D1L3 exhibited similar protein expression levels.

Figure 8A:
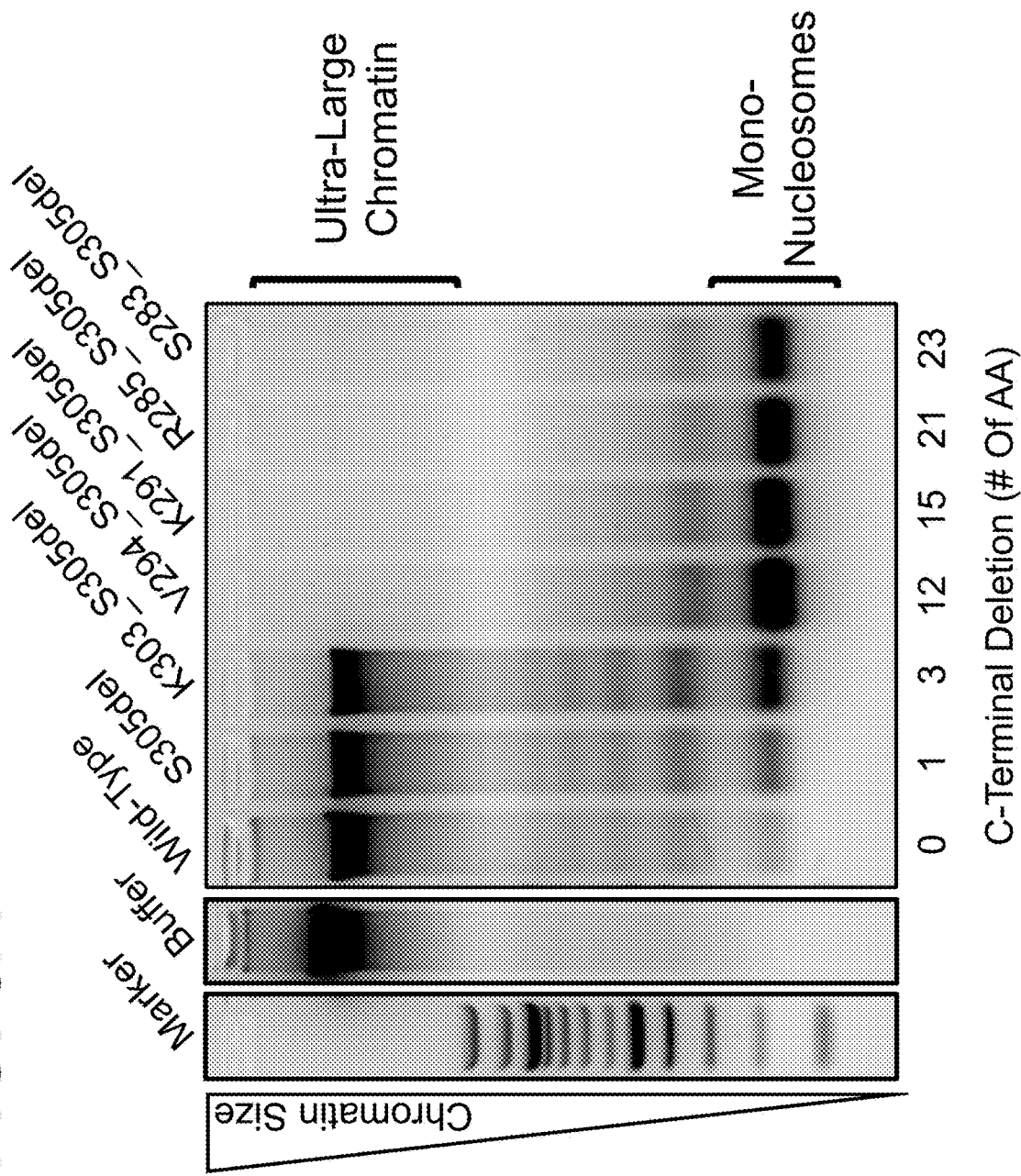
FIG. 8A compares the enzymatic activities of the indicated deletion mutant enzymes with the wild type D1L3 on ultra-large chromatin.
Figure 8B:
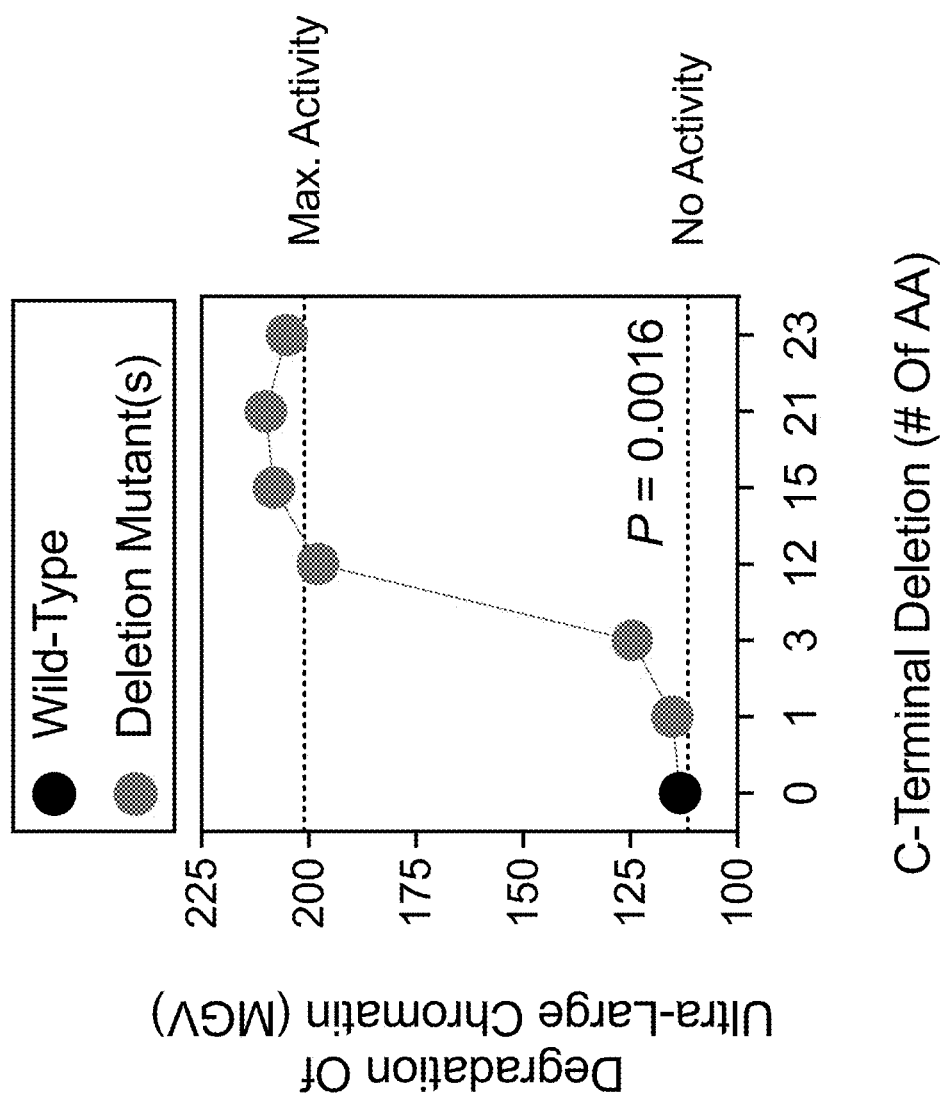
FIG. 8B shows a graph illustrating chromatinase activity of D1L3 as a function length of C-terminal deletion.

The effect of deleting all or part of the BD on chromatin degrading activity was determined by incubating culture supernatants with intact chromatin from isolated nuclei. In the first set of experiments, the culture supernatants of cells expressing wild-type and truncation mutants were diluted 10-fold with incubation buffer and then incubated with high molecular weight chromatin. Analysis of DNA fragmentation by AGE revealed that deletion of 3 or less amino acids caused only a minor increase in enzymatic activity, whereas the deletion of 12 or more amino acids strongly accelerated the degradation of ultra-large chromatin into mono-nucleosomes (FIG. 8A). To quantify chromatin degrading activity, the concentration of ultra-large chromatin, defined as DNA-fragments of >1,500 base pairs, was determined using image analysis of agarose gel electrophoresis (AGE). As shown in FIG. 8B, this analysis confirmed the correlation of BD-deletion and enzymatic activity.

Figure 9B:
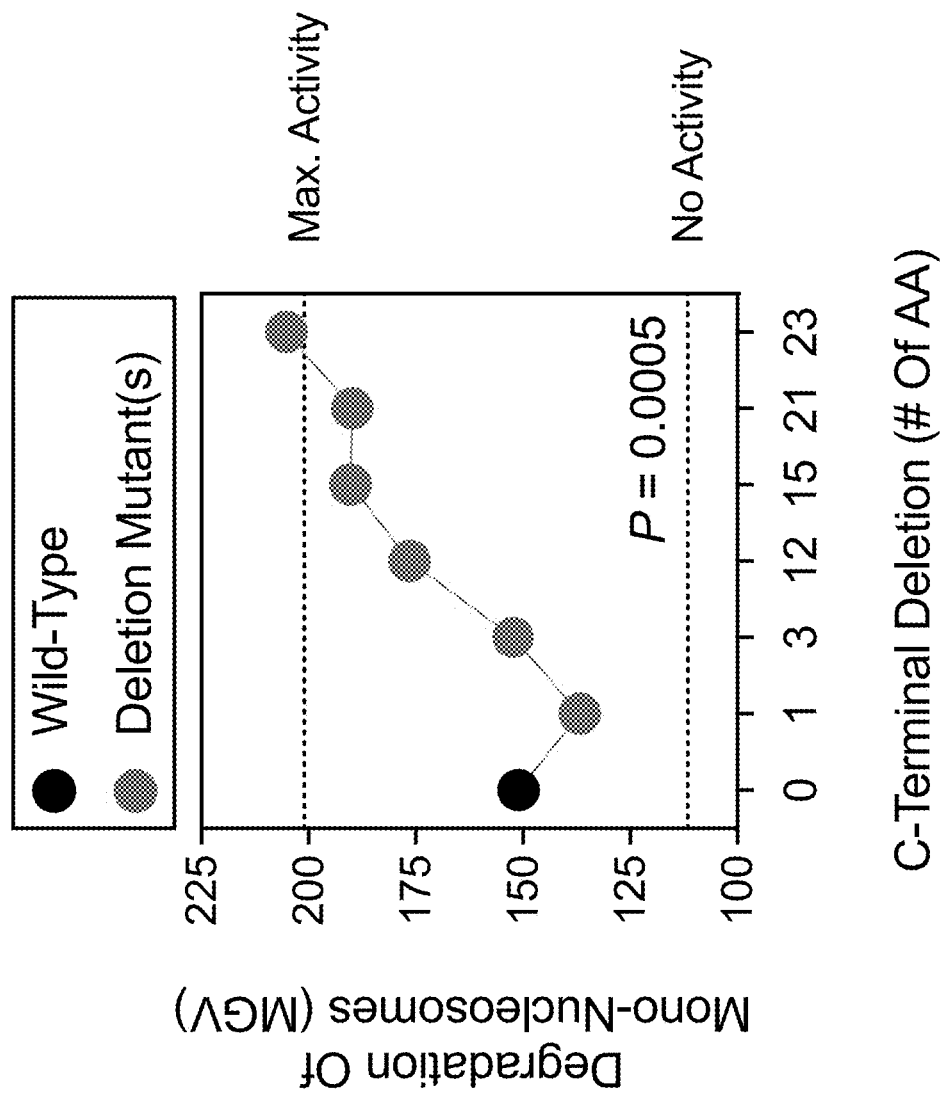
FIG. 9B shows a graph illustrating the degradation of mononucleosomes by the D1L3 mutants as a function length of C-terminal deletion.

In a second set of experiments, undiluted culture supernatants of cells expressing wild-type and truncation mutants were mixed with intact chromatin from isolated nuclei. Under these conditions, ultra-large chromatin was completely degraded into mono-nucleosomes by D1L3 samples (FIG. 9A). Next, mono-nucleosomes, defined as DNA-fragments between 100 and 300 base pairs, were quantified using image analysis. As shown in FIG. 9B, a linear correlation was observed between the deletion of C-terminal amino acids and the activity of D1L3 to degrade mono-nucleosomes. These data showed that enzymatic activity for degrading mononucleosomes increased with increasing length of deletion from three C-terminal amino acids to 23 C-terminal amino acids (FIG. 9B). Taken together, the data illustrate that the entire BD of D1L3 has distinct inhibitory effects on degradation of ultra-large chromatin and mono-nucleosomes.

Example 4: Engineering D1L3 for Large-Scale Manufacturing

Nearly 70% of all biologics are produced using Chinese Hamster Ovary (CHO) cells. Indeed, wild-type DNASE1 (D1; dornase alpha) is typically produced in CHO cells. Despite significant advantages in cell line development and large-scale production using CHO cells, there still remains a significant challenge in the production of Dnase enzymes due to a considerable degree of variability and no reliable methods for predicting or modeling cell growth characteristics. Importantly, CHO cells were not able to stably produce hyperactive variants of D1, which prevented their clinical manufacturing, and the manufacturing properties of other DNASE1-protein family members, including DNASE1-LIKE 3 (D1L3), are largely unknown.

Using CHO and microbial expression systems, several challenges were identified in manufacturing of D1L3, including low production yield, proteolytic degradation, protein misfolding, and erroneous or undesired glycosylation. These are described below.

Figure 10:
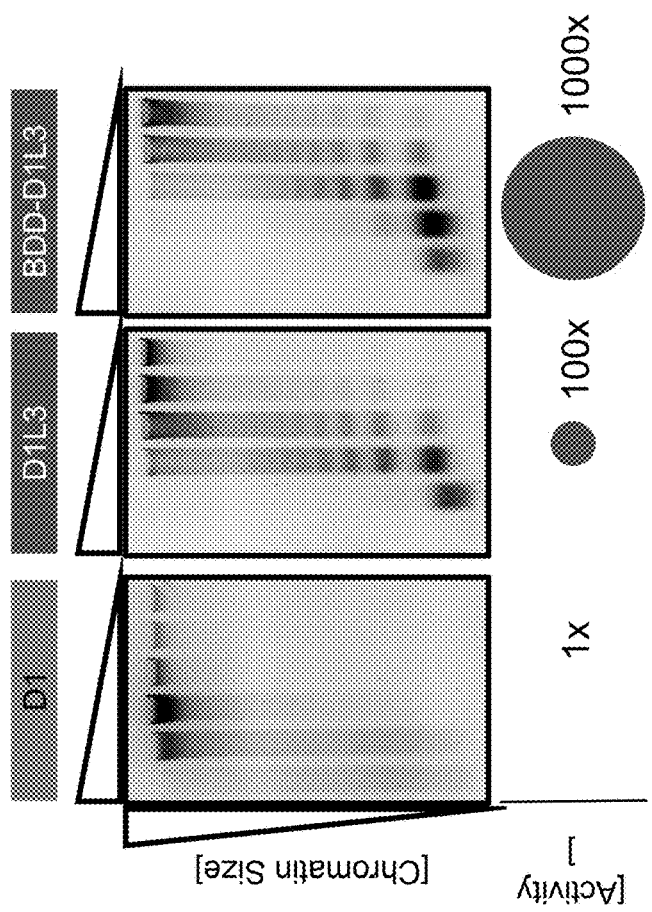
FIG. 10 shows C-terminal amino acid sequences of recombinantly expressed wild-type D1L3 in *Pichia pastoris* to identify frequent cleavage sites. Amino acid sequencing of purified wild-type D1L3 identified three C-terminal deletion mutants: K291_S305del, K292_S305del, and S293_S305del. The C-terminus of wild-type D1L3 was not detected. In parallel, the chromatin degrading activity in the different concentrations of purified protein was analyzed and compared to purified DNASE1 (D1) and the Basic Domain Deleted DNASE1L3 (BDD-D1L3) with a F275Y/F279_K280delinsVM/Q282_S305delinsK mutation. The figure shows DNA analyzed by agarose gel electrophoresis.

*Pichia pastoris* was evaluated as an alternative, microbial expression system to CHO cells. Higher expression levels were generally observed with BDD-D1L3, when compared to wild-type D1L3. Here, we purified and characterized wild-type D1L3 and BDD-D1L3 from *Pichia pastoris* fermentation supernatants (FIG. 10). Unexpectedly, we observed that wild-type D1L3 was proteolytically truncated within the BD at the amino acid positions K291, K291, or S293, leading to a heterogeneous mix of D1L3 variants after purification. Unlike wild-type D1L3, expression of BDD-D1L3 due to three building block substitutions (F275Y, F279_K280delinsVM, Q282_S205delinsK) generated a pure protein.

The chromatinase activity of both D1L3 purifications was compared, where it was observed that the heterogeneous mix of D1L3 variants with BD truncations at positions K291, K291, or S293 had approximately 10-fold lower chromatinase activity compared to the D1L3 variant with a full BD deletion due to F275Y/F279_K280delinsVM/Q282_S205delinsK (FIG. 10). Collectively, the data illustrate that the proteolytic cleavage of the BD can occur naturally in some microbial and mammalian expression systems, and removal of the BD appears to activate D1L3 activity to degrade chromatin.

We attempted to develop a stable CHO cell line producing wild-type D1L3. The cell lines were cultured in bioreactors using standard CHO culture medium. Specifically, FIG. 11 shows a Western Blot of human D1L3 expressed and secreted by CHO cells in a bioreactor under cGMP-compatible conditions. Samples were collected at different time points (t1-t3). Very low levels of D1L3 and D1L3 fragments were detected. The data suggest that low production yield of D1L3 is a challenge in manufacturing of D1L3.

Higher production levels of wild-type D1L3 may be achieved by the addition of polyanions to the culture medium. Such polyanions can comprise one or more of heparin, dextran sulfate, ferric citrate, and ethylenediaminetetraacetic acid, and represent the biologically active ingredient in "anti-cell clumping reagents". Specifically, dextran sulfate was added to the CHO culture medium and an increase was observed in D1L3 as well as D1L3 fragments (FIG. 11). The data illustrate that polyanions can increase production yield of D1L3, but did not prevent proteolytic degradation.

The potential to engineer a protease-resistant D1L3 was also investigated. Wild-type D1L3 contains 50 arginine and lysine residues, which makes the enzyme particularly susceptible to proteases like trypsin, thrombin, and plasmin. In this example, trypsin and plasmin cleavage sites were identified in D1L3 and mutated in an attempt to identify protease-resistance variants of D1L3.

In brief, purified D1L3 was digested with trypsin. D1L3 fragments were isolated, and the amino acid sequence of the fragments determined using combinations of liquid chromatography (LC) and mass spectrometry (MS). It was identified that trypsin cleaved D1L3 at the following arginine and lysine residues: R22, R29, R51, R66, R80, R81, R95, R99, R115, K147, K163, K180, R208, R212, R235, R239, K250, and K262. These arginine and lysine residues might be substituted with small amino acids such as alanine, valine, and serine or with amino acids that have similar properties according to the Grantham's distance score (e.g. histidine, glutamine, and glutamate). D1, which is protease resistant, features arginine and lysine residues corresponding to R51, R95, K99, and R235, suggesting that these residues are not primarily responsible for proteolytic degradation of D1L3.

Building Block Protein Engineering was applied to transfer the following Building Blocks from D1 to replace Building Blocks of D1L3 that contain the trypsin cleavage sites: R22 (Mutation: M21_R22delinsLK), R29 (V28_S30delinsIQT), R66 (N64_I70delinsHLTAVGK), R80 (R77_I83delinsQDAPD), R81 (R77_I83delinsQDAPD), R115 (V113_R115delinsAVD), K163 (K163A), K180 (K180_A181delinsGL), R208 (R208W) MR212 (R212T), R239 (L238_R239delinsVA), K250 (K250D), and K262 (K262G).

Plasmin is a plasma protease that is generated by activation of its zymogen plasminogen. Plasminogen activator inhibitor 1 (PAI-1) inhibits the activation of plasmin. Interestingly, PAI-1 increases the enzymatic activity of D1L3 in serum, suggesting that plasmin may proteolytically inactivate D1L3. However, the plasmin cleavage sites in D1L3 have not been identified.

In silico analysis showed that the amino acid combination lysine-alanine (KA) or arginine-alanine (RA) might be preferably cleaved by the protease plasmin or proteases that have plasmin-like activity. D1L3 contains a total of four putative plasmin-cleavage sites: (Site 1) K180/A181 (K160/A161 without signal peptide), (Site 2) K200/A201 (K180/A181 without signal peptide), (Site 3) K259/A260 (K239/A240 without signal peptide), and (Site 4) R285/A286 (R270/A250 without signal peptide). Using a paired alignment of D1 and D1L3, we found that none of the plasmin cleavage sites are present in D1. The data are in line with the fact that D1 activity is resistant to inactivation by serum proteases, such as thrombin and plasmin. Building Block Protein Engineering was applied to transfer the following Building Blocks from D1 to replace Building Blocks of D1L3 that contain the plasmin cleavage sites: (Site 1) K180_A181delinsGL, (Site 2) P198_A201delinsRPSQ, and (Site 3) K259A. R285/A286 (Site 4) is located in a C-terminal extension that is absent in D1. Consequently, we generated a D1L3 variant in which all four putative plasmin cleavage sites were mutated: K180_A181delinsGL, P198_A201delinsRPSQ, K259A, and R285A. Next, we analyzed chromatin degradation by the D1L3 variant and observed potent chromatin degrading activity in the mutated D1L3. Collectively, the data show that four arginine and lysine residues, K180, K200, K259, and R285, can be mutated to reduce the risk of proteolytic degradation without compromising enzymatic activity.

Next, purified D1L3 was digested with purified plasmin. D1L3 fragments were isolated, and the amino acid sequence of the fragments determined using combinations of LC and MS. We identified that plasmin cleaved D1L3 at the following arginine and lysine residues: R22, R29, K45, K47, K74, R81, R92, K107, K176, R212, R226, R227, K250, K259, and K262. These arginine and lysine residues can be substituted with small amino acids such as alanine, valine, and serine or with amino acids that have similar properties according to the Grantham's distance score (e.g. histidine, glutamine, and glutamate). D1, which is protease resistant, features a lysine residue corresponding to K45, suggesting that this residue is not primarily responsible for proteolytic degradation of D1L3 by plasmin. Building Block Protein Engineering was applied to transfer the following Building Blocks from D1 to replace Building Blocks of D1L3 that contain the trypsin cleavage sites in silico: R22 (Mutation: M21_R22delinsLK), R29 (V28_S30delinsIQT), K47 (K47_K50delinsQILS), K74 (M72_K74delinsLDN), R81 (R77_I83delinsQDAPD), R92 (S91_R92delinsEP), K107 (K107_L110delinsRPDQ), K176 (K176_R178delinsQEK), R212 (R212T), K226 (V225_S228delinsATP), K227 (V225_S228delinsATP), K250 (K250D), K259 (K259A), and K262 (K262G).

Finally, recombinantly expressed wild-type D1L3 was isolated and its C-terminus sequenced. Three different amino acid sequences were identified ending in S290, K291, and K292. The data identify lysine residues 291 and 292 as prominent proteolytic cleavage sites of D1L3 during large-scale manufacturing.

We observed fragmentation of D1L3 after heterologous expression in *Pichia pastoris*. Analysis of the fragments characterized paired basic amino acids, arginine (R) and lysine (K) residues, as proteolytic cleavage sites. A similar degradation pattern was observed after expressing D1L3 in CHO cells. These observations suggest that *Pichia pastoris* and CHO cells share homologous proteases that cleave D1L3 at paired basic amino acids, and the effect was more significant in CHO cells.

It was determined that the paired basic amino acid cleaving enzyme (PACE) contributed to the DNASE1L3 fragmentation. PACE, also known as Furin (Uniprot ID: P09958), is expressed in humans and mammals. *Pichia pastoris* expresses two enzymes, which target paired basic amino acids, namely Aspartic proteinase 3 (Gene: Ysp1; Uniprot ID: P32329) and Kexin (Gene: Kex2; Uniprot ID: P13134).

In addition, mutations of paired basic amino acids in DNASE1L3 and DNASE1L3 variants enable their expression in CHO and *Pichia pastoris* with reduced fragmentation. Analysis of DNASE1L3 fragments identified feature paired basic amino acid at positions: K50/R51, R80/R81, K114/R115, K199/K200, K226/K227, K291/K292, R297/K298/K299, and K303/R304.

Kexin preferably cleaves after KR and RR residues. DNASE1L3 features at K50/R51, R80/R81, K114/R115, and K303/R304 are 4 KEX2-cleavage sites. Amino acid substitutions of these residues render DNASE1L3 resistant to KEX2 and enable the expression of DNASE1L3 and DNASE1L3 variants in *Pichia pastoris* and in CHO cells. These amino acid substitutions can be conservative, e.g. R51K, R81K, R115K, and R304K.

During cGMP-compatible expression of D1L3 in CHO cells, the accumulation of high-molecular weight aggregates of D1L3 was observed, pointing towards an additional challenge for clinical manufacturing D1L3. The high molecular weight aggregates were observed by a lower extent in *Pichia pastoris*.

The application of reducing conditions to proteins of bioreactor material dissolved D1L3 aggregates. The data illustrate that D1L3 aggregate formation is caused by intra- and/or inter-molecular cross-linking via disulfide bridges during protein expression. Specifically, as shown in FIG. 12, the gel was run under non-reducing conditions and shows the accumulation of high-molecular weight aggregates of D1L3 over time. The gel was run under reducing conditions and no aggregates were detected. The data illustrate that erroneous intra- and inter-molecular disulfide bonds cause misfolding of human D1L3 under manufacturing conditions.

Figure 13:
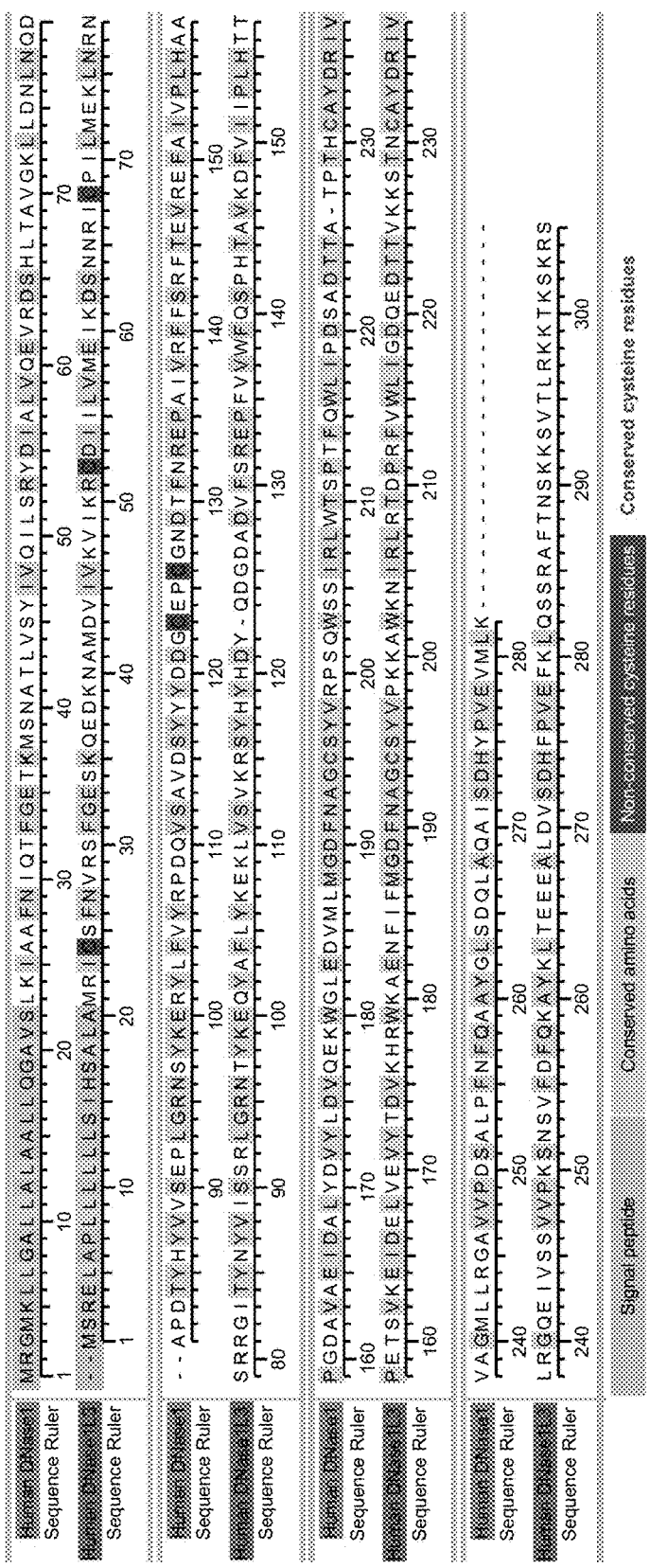
FIG. 13 is an alignment of human D1 (SEQ ID NO: 1) and human D1L3 (SEQ ID NO: 4) amino acid sequences, with conserved and non-conserved cysteine residues shown.

FIG. 13 shows an amino acid sequence alignment of human D1 (SEQ ID NO: 1) and human D1L3 (SEQ ID NO: 4). The signal peptide, conserved amino acids, variable amino acids, non-conserved cysteine residues, and conserved cysteine residues are highlighted. Mutations in non-conserved cysteine residues will reduce the possibilities of intra- and inter-molecular disulfide bonds during protein expression. Analysis of the amino acid sequence of D1L3 showed the presence of five cysteine (C) residues: C24, C52, C68, C194, and C231. The cysteine residues C194 and C231 are conserved among all members of the DNASE1-protein family and form disulfide bonds that are required for enzymatic activity of DNASE1. Accordingly, as disclosed herein, mutation of these cysteine residues reduces the cross-linking via disulfide bridges and thus increases the yield of protein production.

Cysteine residues can be substituted with other small amino acids, namely alanine (A), serine (S), and glycine (G), among others. Such substitutions cause the following amino acid mutations C24A/S/G, C52A/S/G, C68A/S/G, C194A/S/G, and C231A/S/G. In addition, Building Blocks that comprise the conserved cysteine residues can be replaced by Building Blocks from a donor DNase of the DNASE1-protein family (e.g. D1 and D1L3). The following Building Blocks from D1 were used to replace the Building Blocks of D1L3 that contain the non-conserved cysteine residues C24, C52, and C68: C24_S25delinsAA, C52Y, and N64_I70delinsHLTAVGK. The chromatin degrading activity of D1L3 variants was quantified, as described in PCT/US18/4708. Both conventional amino acids substitutions (C24A, C52A) and building block substitutions (C24_S25delinsAA, C52Y) caused a complete absence of chromatin degradation, indicating that C24 and C52 are required for D1L3 activity. Importantly, mutation of cysteine C68, either by conventional amino acid substitution (C68A) or by BB mutation (N64_I70delinsHLTAVGK), resulted in a D1L3 variant with chromatin degrading activity. Amino acid sequence alignment showed that cysteine C68 is not conserved among other DNASE1-protein family members, supporting the notion that C68 is not required for enzymatic activity. Furthermore, it was observed that the amino acid substitution of highly conserved cysteine C194 with alanine (C194A), but not the mutation of the highly conserved cysteine C231 with alanine (C231A), resulted in an enzymatically active D1L3 variant. Thus, cysteine C68 and C194 can be mutated to reduce the risk of erroneous disulfide bonds during D1L3 production.

Example 5: The Paired Basic Amino Acid Cleaving Enzyme Furin Regulates D1L3

The BD domain contains an NLS and three paired basic amino acids that are potentially responsible for the inhibitory effects on enzymatic activity (FIG. 14). The NLS is located between amino acids L286 to S302 [LRKKTKS; Reference: Q13609 (Uniprot)] and therefore absent in all identified hyperactive D1L3 mutants that lack 12 amino acids or more.

Figure 15:
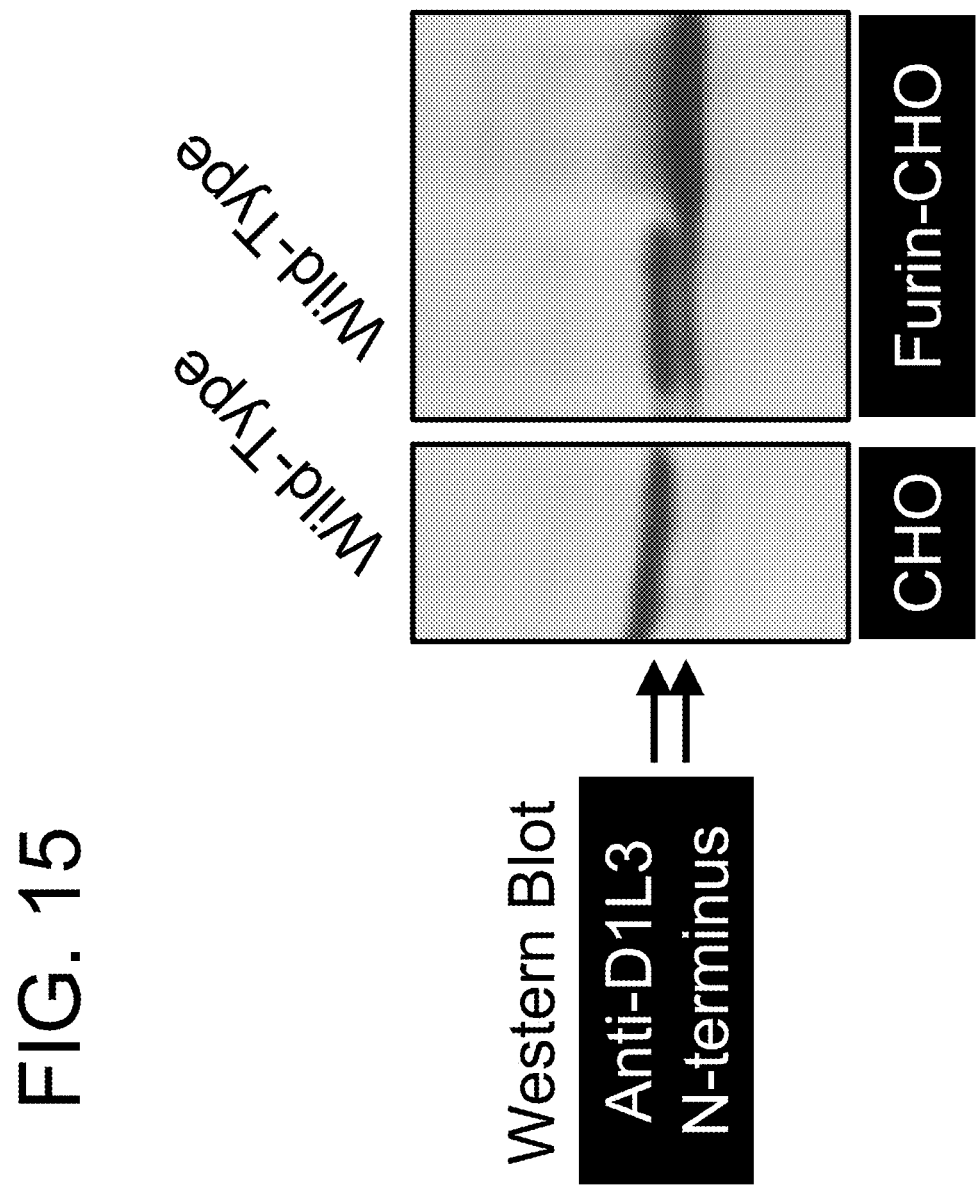
FIG. 15 shows a western blot of wild type D1L3 and BD-deleted D1L3 expressed in furin-overexpressing CHO cells. CHO cells without overexpression of furin were included as control. Data suggest that cleavage of the C-terminal tail or a portion thereof could act as a natural activation signal for D1L3.

It was hypothesized that the three sets of paired basic amino acids (K291/K292, K298/K299, and K303/R304) and may serve as proteolytic cleavage sites of the Paired Basic Amino Acid Cleaving Enzyme (PACE). Furin is a well-characterized PACE, which is involved in the maturation of pro-enzymes. To test the possibility of furin generating active D1L3, and to understand the possible role of furin in activation of chromatinase activity of D1L3, furin-overexpressing CHO cells were transiently transfected with wild-type and BD-deleted D1L3 (S283_S305del mutant). CHO cells without overexpression of furin were included as control. Culture supernatants were collected and tested by western blot using an antibody that targets the N-terminus of D1L3. As shown in FIG. 15, two bands of D1L3 were detected in furin-overexpressing CHO cells. The top band corresponded to D1L3 expressed by CHO cells without overexpression of furin, whereas the lower band corresponded to the BD-deleted D1L3. The data suggest that furin may directly or indirectly delete portions of the BD and thus cause the maturation of D1L3 into its enzymatically active form.

The results disclosed here demonstrate that if D1L3 were expressed in a mammalian cell that provides functional expression of a PACE, such as furin, hyperactive D1L3 could be conveniently administered by cell therapy. Cell therapy is one manner to overcome the numerous challenges in producing D1L3 at large scale, as well as the short half-life of wild-type D1L3, which has a half-life in circulation of less than 30 minutes. Further, white blood cells that migrate to sites of inflammation, cell necrosis and apoptosis, and which can penetrate diseased tissues, could provide an elegant localized chromatinase therapy.

Figure 16:
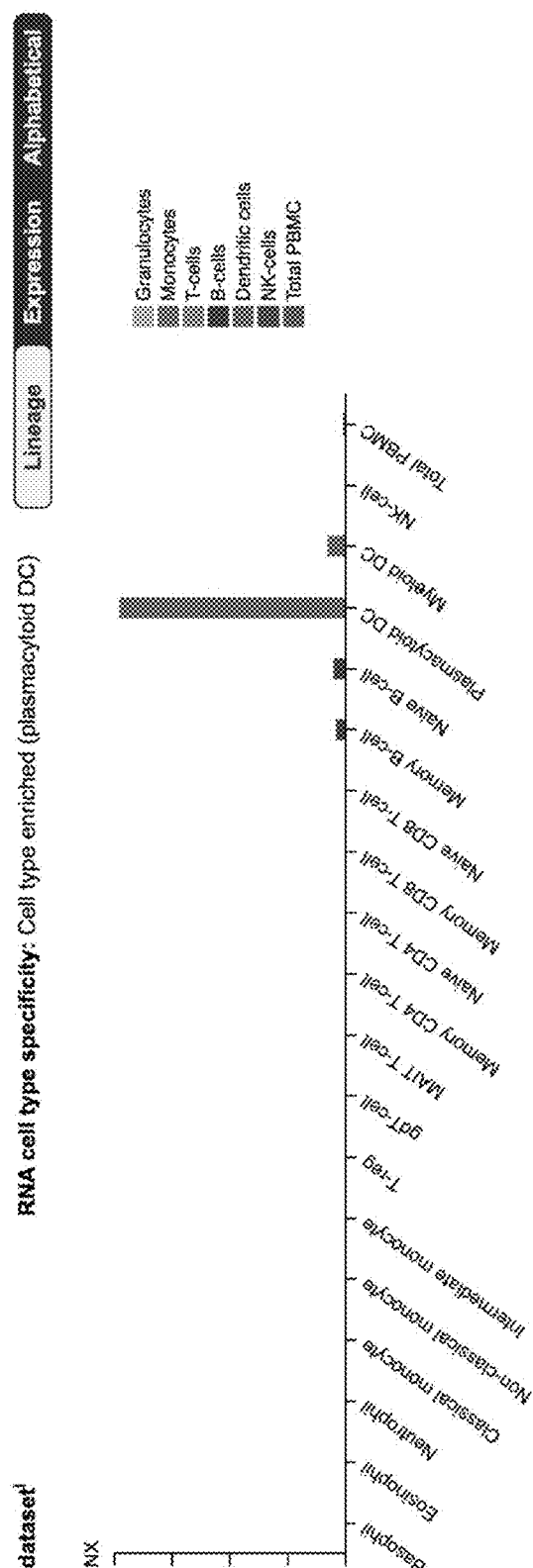
FIG. 16 shows the expression of D1L3 in white blood cell lineages. T cells do not naturally express D1L3 mRNA.
Figure 17:
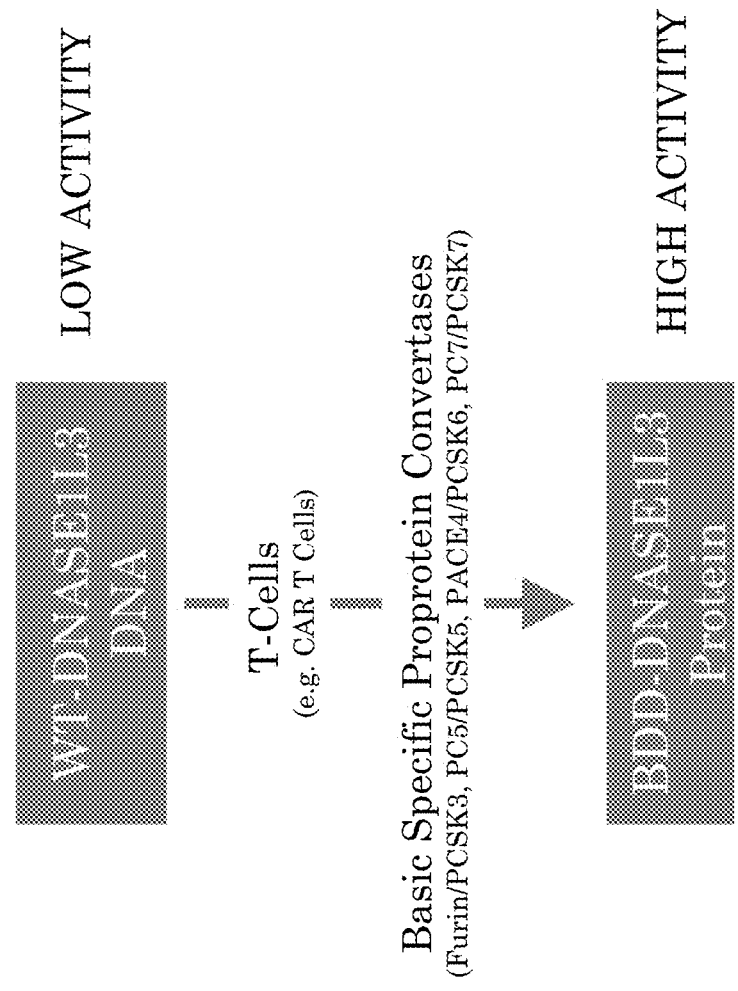
FIG. 17 shows a schematic for D1L3 therapy in connection with T cell therapy. T cells express basic-specific PCSK enzymes that result in the secretion of active enzyme.

Mammalian T cells do not naturally express D1L3 (FIG. 16). However, T cells express several basic-specific Proprotein Convertase Subtilisin/Kexin (PCSK) enzymes, including PCSK types 3, 5, 6, and 7. In fact, activated T-cells specifically induce Furin (PCSK3) expression. See Pesu M, et al., *T-cell-expressed proprotein convertase furin is essential for maintenance of peripheral immune tolerance*, Nature 455, 246-250 (2008). Consequently, the expression of DNASE1L3, including wild-type D1L3 which has low activity) in T-cells will lead to the secretion of an enzymatically hyperactive DNASE1L3 (FIG. 17). This hyperactive variant may be produced at higher levels when the T cells are in an activated state. Further, because T cell therapy, including CAR-T cells, produce large amounts of extracellular chromatin during their action against diseased cells (e.g., cancer or virally-infected cells), D1L3 expression by effector T cells (either CD8+ or CD4+ T cells, or CAR-T cell) can avoid or lessen adverse effects of T cell therapy, such as Tumor Lysis Syndrome. Further still, the pathological presence of NETs in these inflammatory environments can be substantially reduced. Thus, T-cells that express and secret heterologous DNASE1L3 may be used for cell-based therapies in patients in need of extracellular chromatin and/or NET degradation, such as patients with cancer, tumor lysis syndrome, and patients with pneumonia, acute lung injury, or acute respiratory distress syndrome (including COVID-19).

Figure 18:
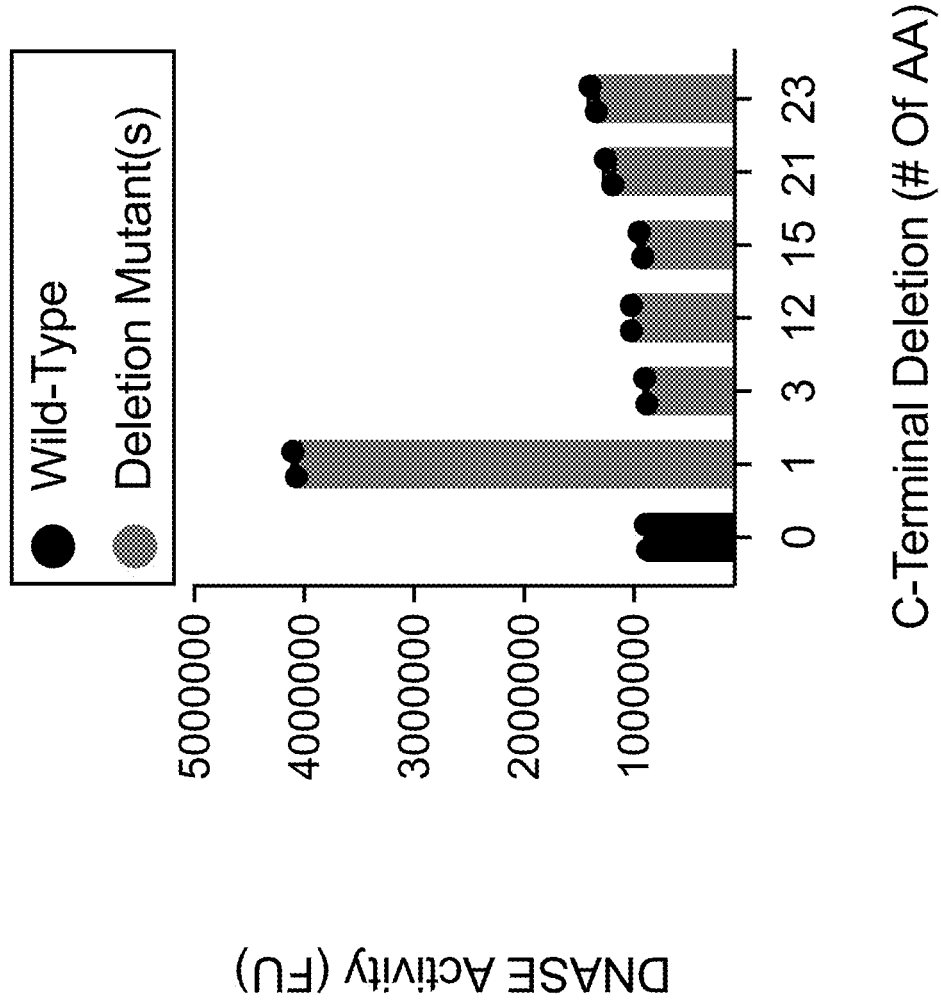
FIG. 18 compares the enzymatic activities of the indicated deletion mutant enzymes with the wild type D1L3 on DNA.

Example 6: Single Amino Acid Deletion Generated D1L3 with Chromatin and DNA-Degrading Activity We tested the activity of the BD-deleted D1L3 mutants to degrade protein-free DNA. In brief, the D1L3-variants were transiently expressed in CHO cells and culture supernatants were incubated with a commercially available DNA-probe, which becomes fluorescent upon cleavage by a DNASE, i.e. DNASEAlert. Surprisingly, we observed a robust increase in DNASE activate upon deletion of the C-terminal serine residue (e.g., S305 of SEQ ID NO:4) (FIG. 18). The deletion of a single amino acid—the C-terminal serine (S305)— generated a DNASE1L3 variant that has chromatinase and high DNASE activity (SEQ ID NO: 22).

```
Wild-Type Human DNASES
DNASE1 (NP_005212.2): Signal Peptide, Mature
Protein:
                                      SEQ ID NO: 1
MRGMKLLGALLALAALLQGAVSLKIAAFNIQTFGETKMSNATLVSYIV

QILSRYDIALVQEVRDSHLTAVGKLLDNLNQDAPDTYHYVVSEPLGRN

SYKERYLFVYRPDQVSAVDSYYYDDGCEPCGNDTFNREPAIVRFFSRF

TEVREFAIVPLHAAPGDAVAEIDALYDVYLDVQEKWGLEDVMLMGDFN

AGCSYVRPSQWSSIRLWTSPTFQWLIPDSADTTATPTHCAYDRIVVAG

MLLRGAVVPDSALPFNFQAAYGLSDQLAQAISDHYPVEVMLK

DNASE1-LIKE 1 (NP_006721.1): Signal Peptide;
Mature Protein:
                                      SEQ ID NO: 2
MHYPTALLFLILANGAQAFRICAFNAQRLTLAKVAREQVMDTLVRILA

RCDIMVLQEVVDSSGSAIPLLLRELNRFDGSGPYSTLSSPQLGRSTYM

ETYVYFYRSHKTQVLSSYVYNDEDDVFAREPFVAQFSLPSNVLPSLVL

VPLHTTPKAVEKELNALYDVFLEVSQHWQSKDVILLGDFNADCASLTK

KRLDKLELRTEPGFHWVIADGEDTTVRASTHCTYDRVVLHGERCRSLL

HTAAAFDFPTSFQLTEEEALNISDHYPVEVELKLSQAHSVQPLSLTVL

LLLSLLSPQLCPAA

DNASE1-LIKE 2 (NP_001365.1): Signal Peptide,
Mature Protein:
                                      SEQ ID NO: 3
MGGPRALLAALWALEAAGTAALRIGAFNIQSFGDSKVSDPACGSILAK

ILAGYDLALVQEVRDPDLSAVSALMEQINSVSEHEYSFVSSQPLGRDQ

YKEMYLFVYRKDAVSVVDTYLYPDPEDVFSREPFVVKFSAPGTGERAP

PLPSRRALTPPPLPAAAQNLVLIPLHAAPHQAVAEIDALYDVYLDVID

KWGTDDMLFLGDFNADCSYVRAQDWAAIRLRSSEVFKWLIPDSADTTV

GNSDCAYDRIVACGARLRRSLKPQSATVHDFQEEFGLDQTQALAISDH

FPVEVTLKFHR

DNASE1-LIKE 3; Isoform 1 (NP_004935.1): Signal
Peptide, Mature Protein:
                                      SEQ ID NO: 4
MSRELAPLLLLLLSIHSALAMRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHFPVEFKLQSSRAFT

NSKKSVTLRKKTKSKRS

DNASE1-LIKE 3, Isoform 2 (NP_001243489.1): Signal
Peptide; Mature Protein:
                                      SEQ ID NO: 5
MSRELAPLLLLLLSIHSALAMRICSFNVRSFGESKQEDKNAMDVIVKV

IKRCDIILVMEIKDSNNRICPILMEKLNREKLVSVKRSYHYHDYQDGD

ADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQED

TTVKKSTNCAYDRIVLRGQEIVSSVVPKSNSVFDFQKAYKLTEEEALD

VSDHFPVEFKLQSSRAFTNSKKSVTLRKKTKSKRS
```

DNASE2A (O00115): <u>Signal Peptide</u>; Mature Protein:
SEQ ID NO: 6

<u>MIPLLLAALLCVPAGAL</u>TCYGDSGQPVDWFVVYKLPALRGSGEAAQRG

LQYKYLDESSGGWRDGRALINSPEGAVGRSLQPLYRSNTSQLAFLLYN

DQPPQPSKAQDSSMRGHTKGVLLLDHDGGFWLVHSVPNFPPPASSAAY

SWPHSACTYGQTLLCVSFPFAQFSKMGKQLTYTYPWVYNYQLEGIFAQ

EFPDLENVVKGHHVSQEPWNSSITLTSQAGAVFQSFAKFSKFGDDLYS

GWLAAALGTNLQVQFWHKTVGILPSNCSDIWQVLNVNQIAFPGPAGPS

FNSTEDHSKWCVSPKGPWICVGDMNRNQGEEQRGGGILCAQLPALWKA

FQPLVKNYQPCNGMARKPSRAYKI

DNASE2B (Q8WZ79): <u>Signal Peptide</u>; Mature Protein:
SEQ ID NO: 7

<u>MKQKMMARLLRTSFALLFLGLFGVLGA</u>ATISCRNEEGKAVDWFTFYKL

PKRQNKESGETGLEYLYLDSTTRSWRKSEQLMNDTKSVLGRTLQQLYE

AYASKSNNTAYLIYNDGVPKPVNYSRKYGHTKGLLLWNRVQGFWLIHS

IPQFPPIPEEGYDYPPTGRRNGQSGICITFKYNQYEAIDSQLLVCNPN

VYSCSIPATFHQELIHMPQLCTRASSSEIPGRLLTTLQSAQGQKFLHF

AKSDSFLDDIFAAWMAQRLKTHLLTETWQRKRQELPSNCSLPYHVYNI

KAIKLSRHSYFSSYQDHAKWCISQKGTKNRWTCIGDLNRSPHQAFRSG

GFICTQNWQIYQAFQGLVLYYESCK

Chimeras of Human DNASE1L3 and DNASE1
D1L3 + D1-BB#50: <u>Signal Peptide</u>; Mature
Protein (Building block transferred from D1):
SEQ ID NO: 8

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTATPTNCAYDRIVLRGQ

EIVSSVVPKSNSVFDFQKAYKLTEEEALDVSDHFPVEFKLQSSRAFTN

SKKSVTLRKKTKSKRS

D1L3 + D1-BB#51: <u>Signal Peptide</u>; Mature
Protein (Building block transferred from D1):
SEQ ID NO: 9

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSTHCAYDRIVLRG

QEIVSSVVPKSNSVFDFQKAYKLTEEEALDVSDHFPVEFKLQSSRAFT

NSKKSVTLRKKTKSKRS

D1L3 + D1-BB#52: <u>Signal Peptide</u>; Mature
Protein (Building block transferred from D1):
SEQ ID NO: 10

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVVAG

QEIVSSVVPKSNSVFDFQKAYKLTEEEALDVSDHFPVEFKLQSSRAFT

NSKKSVTLRKKTKSKRS

D1L3 + D1-BB#53: <u>Signal Peptide</u>; Mature
Protein (Building block transferred from D1):
SEQ ID NO: 11

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

MLLRGAVVPKSNSVFDFQKAYKLTEEEALDVSDHFPVEFKLQSSRAFT

NSKKSVTLRKKTKSKRS

D1L3 + D1-BB#54: <u>Signal Peptide</u>; Mature
Protein (Building block transferred from D1):
SEQ ID NO: 12

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPDSNSVFDFQKAYKLTEEEALDVSDHFPVEFKLQSSRAFT

NSKKSVTLRKKTKSKRS

D1L3 + D1-BB#55: <u>Signal Peptide</u>; Mature
Protein (Building block transferred from D1):
SEQ ID NO: 13

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNALPDFQKAYKLTEEEALDVSDHFPVEFKLQSSRAFT

NSKKSVTLRKKTKSKRS

D1L3 + D1-BB#56: <u>Signal Peptide</u>; Mature
Protein (Building block transferred from D1):
SEQ ID NO: 14

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYHDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFNFQKAYKLTEEEALDVSDHFPVEFKLQSSRAFT

NSKKSVTLRKKTKSKRS

D1L3 + D1-BB#57: <u>Signal Peptide</u>; Mature
Protein (Building block transferred from D1):
SEQ ID NO: 15

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQAAYKLTEEEALDVSDHFPVEFKLQSSRAFT

NSKKSVTLRKKTKSKRS

D1L3 + D1-BB#58: <u>Signal Peptide</u>; Mature
Protein (Building block transferred from D1):
SEQ ID NO: 16

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYGLTEEEALDVSDHFPVEFKLQSSRAFT

NSKKSVTLRKKTKSKRS

D1L3 + D1-BB#59: <u>Signal Peptide</u>; Mature
Protein (Building block transferred from D1):
SEQ ID NO: 17

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLSDQLALDVSDHFPVEFKLQSSRAFT

NSKKSVTLRKKTKSKRS

D1L3 + D1-BB#60: <u>Signal Peptide</u>; Mature
Protein (Building block transferred from D1):
SEQ ID NO: 18

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEAQAISDHFPVEFKLQSSRAFT

NSKKSVTLRKKTKSKRS

D1L3 + D1-BB#61: <u>Signal Peptide</u>; Mature
Protein (Building block transferred from D1):
SEQ ID NO: 19

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHYPVEFKLQSSRAFT

NSKKSVTLRKKTKSKRS

D1L3 + D1-BB#62: <u>Signal Peptide</u>; Mature
Protein (Building block transferred from D1):
SEQ ID NO: 20

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHFPVEVMLQSSRAFT

NSKKSVTLRKKTKSKRS

D1L3 + D1-BB#63: <u>Signal Peptide</u>; Mature
Protein (Building block transferred from D1):
SEQ ID NO: 21

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHFPVEFKLK

C-terminal deletion mutants of Human DNASE1L3
S305del: <u>Signal Peptide</u>; Mature Protein:
SEQ ID NO: 22

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHFPVEFKLQSSRAFT

NSKKSVTLRKKTKSKR

K303_S305del: <u>Signal Peptide</u>; Mature Protein:
SEQ ID NO: 23

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHFPVEFKLQSSRAFT

NSKKSVTLRKKTKS

V294_S305del: <u>Signal Peptide</u>; Mature Protein:
SEQ ID NO: 24

<u>MSRELAPLLLLLLSIHSALA</u>MRICSFNVRSFGESKQEDKNAMDVIVKV

IKRCDIILVMEIKDSNNRICPILMEKLNRNSRRGITYNYVISSRLGRN

TYKEQYAFLYKEKLVSVKRSYHYDYQDGDADVFSREPFVVWFQSPHT

AVKDFVIIPLHTTPETSVKEIDELVEVYTDVKHRWKAENFIFMGDFNA

GCSYVPKKAWKNIRLRTDPRFVWLIGDQEDTTVKKSINCAYDRIVLRG

QEIVSSVVPKSNSVFDFQKAYKLTEEEALDVSDHFPVEFKLQSSRAFT

NSKKS

K291_S305del: Signal Peptide; Mature Protein:
SEQ ID NO: 25
MSRELAPLLLLLLSIHSALAMRICSFNVRSFGESKQEDKNAMDVIVKV
IKRCDIILVMEIKDSNNRICPILMEKLNRNSRRGITYNYVISSRLGRN
TYKEQYAFLYKEKLVSVKRSYHYDYQDGDADVFSREPFVVWFQSPHT
AVKDFVIIPLHTTPETSVKEIDELVEVYTDVKHRWKAENFIFMGDFNA
GCSYVPKKAWKNIRLRTDPRFVWLIGDQEDTTVKKSINCAYDRIVLRG
QEIVSSVVPKSNSVFDFQKAYKLTEEEALDVSDHFPVEFKLQSSRAFT
NS R285_S305del: Signal Peptide; Mature Protein:
SEQ ID NO: 26
MSRELAPLLLLLLSIHSALAMRICSFNVRSFGESKQEDKNAMDVIVKV
IKRCDIILVMEIKDSNNRICPILMEKLNRNSRRGITYNYVISSRLGRN
TYKEQYAFLYKEKLVSVKRSYHYDYQDGDADVFSREPFVVWFQSPHT
AVKDFVIIPLHTTPETSVKEIDELVEVYTDVKHRWKAENFIFMGDFNA
GCSYVPKKAWKNIRLRTDPRFVWLIGDQEDTTVKKSINCAYDRIVLRG
QEIVSSVVPKSNSVFDFQKAYKLTEEEALDVSDHFPVEFKLQSS S283_S305del: Signal Peptide; Mature Protein:
SEQ ID NO: 27
MSRELAPLLLLLLSIHSALAMRICSFNVRSFGESKQEDKNAMDVIVKV
IKRCDIILVMEIKDSNNRICPILMEKLNRNSRRGITYNYVISSRLGRN
TYKEQYAFLYKEKLVSVKRSYHYDYQDGDADVFSREPFVVWFQSPHT
AVKDFVIIPLHTTPETSVKEIDELVEVYTDVKHRWKAENFIFMGDFNA
GCSYVPKKAWKNIRLRTDPRFVWLIGDQEDTTVKKSINCAYDRIVLRG
QEIVSSVVPKSNSVFDFQKAYKLTEEEALDVSDHFPVEFKLQ SIGNAL PEPTIDES
Alpha mating factor (P01149):
SEQ ID NO: 28
MRFPSIFTAVLFAASSALAAPVNTTTEDETAQIPAEAVIGYSDLEGDF
DVAVLPFSNSTNNGLLFINTTIASIAAKEEGVS Human Albumin Secretory Signal Peptide + Propeptide (P02768):
SEQ ID NO: 29
MKWVTFISLLFLFSSAYSRGVFRR Human DNASE1L3 Signal Peptide (Q13609):
SEQ ID NO: 30
MSRELAPLLLLLLSIHSALA

LINKER SEQUENCES
SEQ ID NO: 31
GGGGS

SEQ ID NO: 32
GGGGSGGGGSGGGGS

SEQ ID NO: 33
APAPAPAPAPAPAP

SEQ ID NO: 34
AEAAAKEAAAKA

SEQ ID NO: 35
SGGSGSS

SEQ ID NO: 36
SGGSGGSGGSGGSSS

SEQ ID NO: 37
SGGSGGSGGSGGSGGSGGSGGSGGSGGSGGSSS

SEQ ID NO: 38
GGSGGSGGSGGSGGSGGSGGSGGSGGSGS

OTHER SEQUENCES
Human Serum Albumin (Mature Protein):
SEQ ID NO: 39
DAHKSEVAHRFKDLGEENFKALVLIAFAQYLQQCPFEDHVKLVNEVTE
FAKTCVADESAENCDKSLHTLFGDKLCTVATLRETYGEMADCCAKQEP
ERNECFLQHKDDNPNLPRLVRPEVDVMCTAFHDNEETFLKKYLYEIAR
RHPYFYAPELLFFAKRYKAAFTECCQAADKAACLLPKLDELRDEGKAS
SAKQRLKCASLQKFGERAFKAWAVARLSQRFPKAEFAEVSKLVTDLTK
VHTECCHGDLLECADDRADLAKYICENQDSISSKLKECCEKPLLEKSH
CIAEVENDEMPADLPSLAADFVESKDVCKNYAEAKDVFLGMFLYEYAR
RHPDYSVVLLLRLAKTYETTLEKCCAAADPHECYAKVFDEFKPLVEEP
QNLIKQNCELFEQLGEYKFQNALLVRYTKKVPQVSTPTLVEVSRNLGK
VGSKCCKHPEAKRMPCAEDYLSVVLNQLCVLHEKTPVSDRVTKCCTES
LVNRRPCFSALEVDETYVPKEFNAETFTFHADICTLSEKERQIKKQTA
LVELVKHKPKATKEQLKAVMDDFAAFVEKCCKADDKETCFAEEGKKLV
AASQAALGL Human Factor XI:
SEQ ID NO: 40
MIFLYQVVHFILFTSVSGECVTQLLKDTCFEGGDITTVFTPSAKYCQV
VCTYHPRCLLFTFTAESPSEDPTRWFTCVLKDSVTETLPRVNRTAAIS
GYSFKQCSHQISACNKDIYVDLDMKGINYNSSVAKSAQECQERCTDDV
HCHFFTYATRQFPSLEHRNICLLKHTQTGTPTRITKLDKVVSGFSLKS
CALSNLACIRDIFPNTVFADSNIDSVMAPDAFVCGRICTHHPGCLFFT
FFSQEWPKESQRNLCLLKTSESGLPSTRIKKSKALSGFSLQSCRHSIP
VFCHSSFYHDTDFLGEELDIVAAKSHEACQKLCTNAVRCQFFTYTPAQ
ASCNEGKGKCYLKLSSNGSPTKILHGRGGISGYTLRLCKMDNECTTKI
KPRIVGGTASVRGEWPWQVTLHITSPTQRHLCGGSIIGNQWILTAAHC
FYGVESPKILRVYSGILNQSEIKEDTSFFGVQEIIIHDQYKMAESGYD
IALLKLETTVNYTDSQRPICLPSKGDRNVIYTDCWVTGWGYRKLRDKI
QNTLQKAKIPLVTNEECQKRYRGHKITHKMICAGYREGGKDACKGDSG
GPLSCKHNEVWHLVGITSWGEGCAQRERPGVYTNVVEYVDWILEKTQAV Human prekallikrein:
SEQ ID NO: 41
MILFKQATYFISLLFATVSCGCLTQLYENAFFRGGDVASMYTPNAQYCQ
MRCTFHPRCLLFSFLPASSINDMEKRFGCFLKDSVTGILPKVHRTGAV
SGHSLKQCGHQISACHRDIYKGVDMRGVNFNVSKVSSVEECQKRCTNN
IRCQFFSYATQTFHKAEYRNNCLLKYSPGGTPTAIKVLSNVESGFSLK
PCALSEIGCHMNIFQHLAFSDVDVARVLTPDAFVCRTICTYHPNCLFF
TFYTNVWKIESQRNVCLLKTSESGTPSSSTPQENTISGYSLLICKRTL
PEPCHSKIYPGVDFGGEELNVTFVKGVNVCQETCTKMIRCQFFTYSLL
PEDCKEEKCKCFLRLSMDGSPTRIAYGTQGSSGYSLRLCNTGDNSVCT -continued

IKTSTRIVGGINSSWGEWPWQVSLQVKLTAQRHLCGGSLIGHQWVLTA

AHCFDGLPLQDVWRIYSGILNLSDITKDTPFSQIKEIIIHQNYKVSEG

NHDIALIKLQAPLNYTEFQKPICLPSKGDTSTIYTNCWVTGWGFSKEK

GEIQNILQKVNIPLVTNEECQKRYQDYKITQRMVCAGYKEGGKDACKG

DSGGPLVCKHNGMWRLVGITSWGEGCARREQPGVYTKVAEYMDWILEK

TQSSDGKAQMQSPA

DNase epitope

SEQ ID NO: 42

MGDFNAGCSYV

ACTIVATABLE LINKER SEQUENCES

FXIIa-susceptible linker (Factor XI peptide):

SEQ ID NO: 43

CTTKIKPRIVGGTASVRGEWPWQVT

FXIIa-susceptible linker

SEQ ID NO: 44

GGGGSPRIGGGGS

FXIIa-susceptible linker (Prekallikrein peptide):

SEQ ID NO: 45

VCTIKTSTRIVGGINSSWGEWPWQVS

FXIIa-susceptible linker (Prekallikrein peptide):

SEQ ID NO: 46

STRIVGG

FUSIONS BETWEEN ALBUMIN AND BD-DELETED D1L3

Albumin - DNASE1L3 Variant - Fusion Protein.
(Albumin, DNASE1L3 Variant):

SEQ ID NO: 47

-continued

DAHKSEVAHRFKDLGEENFKALVLIAFAQYLQQCPFEDHVKLVNEVTE

FAKTCVADESAENCDKSLHTLFGDKLCTVATLRETYGEMADCCAKQEP

ERNECFLQHKDDNPNLPRLVRPEVDVMCTAFHDNEETFLKKYLYEIAR

RHPYFYAPELLFFAKRYKAAFTECCQAADKAACLLPKLDELRDEGKAS

SAKQRLKCASLQKFGERAFKAWAVARLSQRFPKAEFAEVSKLVTDLTK

VHTECCHGDLLECADDRADLAKYICENQDSISSKLKECCEKPLLEKSH

CIAEVENDEMPADLPSLAADFVESKDVCKNYAEAKDVFLGMFLYEYAR

RHPDYSVVLLLRLAKTYETTLEKCCAADPHECYAKVFDEFKPLVEEP

QNLIKQNCELFEQLGEYKFQNALLVRYTKKVPQVSTPTLVEVSRNLGK

VGSKCCKHPEAKRMPCAEDYLSVVLNQLCVLHEKTPVSDRVTKCCTES

LVNRRPCFSALEVDETYVPKEFNAETFTFHADICTLSEKERQIKKQTA

LVELVKHKPKATKEQLKAVMDDFAAFVEKCCKADDKETCFAEEGKKLV

AASQAALGLSGGSGGSGGSGGSGGSGGSGGSGGSGGSGSSMRICSFNV

RSFGESKQEDKNAMDVIVKVIKRCDIILVMEIKDSNNRICPILMEKLN

RNSRRGITYNYVISSRLGRNTYKEQYAFLYKEKLVSVKRSYHYHDYQD

GDADVFSREPFVVWFQSPHTAVKDFVIIPLHTTPETSVKEIDELVEVY

TDVKHRWKAENFIFMGDFNAGCSYVPKKAWKNIRLRTDPRFVWLIGDQ

EDTTVKKSTNCAYDRIVLRGQEIVSSVVPKSNSVFDFQKAYKLTEEEA

LDVSDHFPVEFKLQ

What is claimed is:

1. A method for treating a subject having cancer, the method comprising administering a composition comprising isolated T cells to the subject, the isolated T cells being modified in vitro to express a heterologous polynucleotide encoding a DNASE1-LIKE 3 (D1L3) enzyme,
    wherein the encoded D1L3 enzyme comprises an amino acid sequence that has at least 95% sequence identity to amino acids 21 to 282 of SEQ ID NO: 4 or amino acids 21 to 252 of SEQ ID NO: 5, and comprises a C-terminal basic domain comprising a nuclear localization signal;
    wherein the polynucleotide is DNA operably linked to a promoter or is mRNA
    wherein the isolated T cells secrete the D1L3 enzyme, and
    wherein the secreted D1L3 enzyme has at least a partial truncation of the C-terminal basic domain and has chromatin-degrading activity.

2. The method of claim 1, wherein the secreted D1L3 enzyme has a truncation of at least 12 amino acids of the C-terminal basic domain.

3. The method of claim 2, wherein the C-terminal basic domain of the secreted D1L3 enzyme lacks the amino acids corresponding to (i) residues 291 to 305 of SEQ ID NO: 4, (ii) residues 292 to 305 of SEQ ID NO: 4, or (iii) residues 293 to 305 of SEQ ID NO: 4.

4. The method of claim 1, wherein the heterologous polynucleotide is DNA.

5. The method of claim 1, wherein the heterologous polynucleotide is an mRNA, which is optionally a modified mRNA (mmRNA).

6. The method of claim 1, wherein the polynucleotide is introduced to the cell using a viral vector.

7. The method of claim 1, wherein the polynucleotide is introduced to the cell using a gene-editing system selected from CRISPR-Cas9, zinc finger nuclease, or transcription activator-like effector nucleases (TALENS).

8. The method of claim 1, wherein the D1L3 enzyme comprises an amino acid sequence that has at least 97% sequence identity to amino acids 21 to 282 of the enzyme of SEQ ID NO: 4 or amino acids 21 to 252 of SEQ ID NO: 5.

9. The method of claim 1, wherein the D1L3 enzyme is fused to a carrier protein.

10. The method of claim 9, wherein the carrier protein is albumin.

11. The method of claim 9, wherein the D1L3 enzyme is fused to the carrier protein at the N-terminus of the D1L3 enzyme through a flexible or cleavable linker.

12. The method of claim 1, wherein the subject is at risk of vascular occlusions involving extracellular chromatin released by cancer cells or injured endothelial cells.

13. The method of claim 12, wherein the cancer is leukemia.

14. The method of claim 12, wherein the cancer is a solid tumor.

15. The method of claim 14, wherein the tumor is metastatic.

16. The method of claim 1, wherein the T cells express a Chimeric Antigen Receptor (CAR).

17. The method of claim 1, wherein the T cells are central memory T cells and/or effector memory T cells.

18. The method of claim 1, wherein the T cells are predominately terminally differentiated.

\* \* \* \* \*

SEQUENCE LISTING

<160> NUMBER OF SEQ ID NOS: 47

<210> SEQ ID NO 1
<211> LENGTH: 282
<212> TYPE: PRT
<213> ORGANISM: Homo sapiens

<400> SEQUENCE: 1

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140
```

```
Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
            245                 250                 255

Phe Gln Ala Ala Tyr Gly Leu Ser Asp Gln Leu Ala Gln Ala Ile Ser
        260                 265                 270

Asp His Tyr Pro Val Glu Val Met Leu Lys
        275                 280

<210> SEQ ID NO 2
<211> LENGTH: 302
<212> TYPE: PRT
<213> ORGANISM: Homo sapiens

<400> SEQUENCE: 2

Met His Tyr Pro Thr Ala Leu Leu Phe Leu Ile Leu Ala Asn Gly Ala
1               5                   10                  15

Gln Ala Phe Arg Ile Cys Ala Phe Asn Ala Gln Arg Leu Thr Leu Ala
            20                  25                  30

Lys Val Ala Arg Glu Gln Val Met Asp Thr Leu Val Arg Ile Leu Ala
        35                  40                  45

Arg Cys Asp Ile Met Val Leu Gln Glu Val Val Asp Ser Ser Gly Ser
50                  55                  60

Ala Ile Pro Leu Leu Leu Arg Glu Leu Asn Arg Phe Asp Gly Ser Gly
65                  70                  75                  80

Pro Tyr Ser Thr Leu Ser Ser Pro Gln Leu Gly Arg Ser Thr Tyr Met
            85                  90                  95

Glu Thr Tyr Val Tyr Phe Tyr Arg Ser His Lys Thr Gln Val Leu Ser
            100                 105                 110

Ser Tyr Val Tyr Asn Asp Glu Asp Val Phe Ala Arg Glu Pro Phe
        115                 120                 125

Val Ala Gln Phe Ser Leu Pro Ser Asn Val Leu Pro Ser Leu Val Leu
130                 135                 140

Val Pro Leu His Thr Thr Pro Lys Ala Val Glu Lys Glu Leu Asn Ala
145                 150                 155                 160

Leu Tyr Asp Val Phe Leu Glu Val Ser Gln His Trp Gln Ser Lys Asp
            165                 170                 175

Val Ile Leu Leu Gly Asp Phe Asn Ala Asp Cys Ala Ser Leu Thr Lys
        180                 185                 190

Lys Arg Leu Asp Lys Leu Glu Leu Arg Thr Glu Pro Gly Phe His Trp
        195                 200                 205

Val Ile Ala Asp Gly Glu Asp Thr Thr Val Arg Ala Ser Thr His Cys
210                 215                 220

Thr Tyr Asp Arg Val Val Leu His Gly Glu Arg Cys Arg Ser Leu Leu
225                 230                 235                 240
```

```
His Thr Ala Ala Ala Phe Asp Phe Pro Thr Ser Phe Gln Leu Thr Glu
            245                 250                 255

Glu Glu Ala Leu Asn Ile Ser Asp His Tyr Pro Val Glu Val Glu Leu
        260                 265                 270

Lys Leu Ser Gln Ala His Ser Val Gln Pro Leu Ser Leu Thr Val Leu
    275                 280                 285

Leu Leu Leu Ser Leu Leu Ser Pro Gln Leu Cys Pro Ala Ala
290                 295                 300

<210> SEQ ID NO 3
<211> LENGTH: 299
<212> TYPE: PRT
<213> ORGANISM: Homo sapiens

<400> SEQUENCE: 3

Met Gly Gly Pro Arg Ala Leu Leu Ala Leu Trp Ala Leu Glu Ala
1               5                   10                  15

Ala Gly Thr Ala Ala Leu Arg Ile Gly Ala Phe Asn Ile Gln Ser Phe
            20                  25                  30

Gly Asp Ser Lys Val Ser Asp Pro Ala Cys Gly Ser Ile Ile Ala Lys
        35                  40                  45

Ile Leu Ala Gly Tyr Asp Leu Ala Leu Val Gln Glu Val Arg Asp Pro
    50                  55                  60

Asp Leu Ser Ala Val Ser Ala Leu Met Glu Gln Ile Asn Ser Val Ser
65                  70                  75                  80

Glu His Glu Tyr Ser Phe Val Ser Ser Gln Pro Leu Gly Arg Asp Gln
                85                  90                  95

Tyr Lys Glu Met Tyr Leu Phe Val Tyr Arg Lys Asp Ala Val Ser Val
            100                 105                 110

Val Asp Thr Tyr Leu Tyr Pro Asp Pro Glu Asp Val Phe Ser Arg Glu
        115                 120                 125

Pro Phe Val Val Lys Phe Ser Ala Pro Gly Thr Gly Glu Arg Ala Pro
    130                 135                 140

Pro Leu Pro Ser Arg Arg Ala Leu Thr Pro Pro Pro Leu Pro Ala Ala
145                 150                 155                 160

Ala Gln Asn Leu Val Leu Ile Pro Leu His Ala Ala Pro His Gln Ala
                165                 170                 175

Val Ala Glu Ile Asp Ala Leu Tyr Asp Val Tyr Leu Asp Val Ile Asp
            180                 185                 190

Lys Trp Gly Thr Asp Asp Met Leu Phe Leu Gly Asp Phe Asn Ala Asp
        195                 200                 205

Cys Ser Tyr Val Arg Ala Gln Asp Trp Ala Ala Ile Arg Leu Arg Ser
    210                 215                 220

Ser Glu Val Phe Lys Trp Leu Ile Pro Asp Ser Ala Asp Thr Thr Val
225                 230                 235                 240

Gly Asn Ser Asp Cys Ala Tyr Asp Arg Ile Val Ala Cys Gly Ala Arg
                245                 250                 255

Leu Arg Arg Ser Leu Lys Pro Gln Ser Ala Thr Val His Asp Phe Gln
            260                 265                 270

Glu Glu Phe Gly Leu Asp Gln Thr Gln Ala Leu Ala Ile Ser Asp His
        275                 280                 285

Phe Pro Val Glu Val Thr Leu Lys Phe His Arg
    290                 295
```

```
<210> SEQ ID NO 4
<211> LENGTH: 305
<212> TYPE: PRT
<213> ORGANISM: Homo sapiens

<400> SEQUENCE: 4

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305

<210> SEQ ID NO 5
<211> LENGTH: 275
<212> TYPE: PRT
<213> ORGANISM: Homo sapiens

<400> SEQUENCE: 5

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
```

```
            20                  25                  30
Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Glu Lys Leu
 65                  70                  75                  80

Val Ser Val Lys Arg Ser Tyr His Tyr His Asp Tyr Gln Asp Gly Asp
                85                  90                  95

Ala Asp Val Phe Ser Arg Glu Pro Phe Val Val Trp Phe Gln Ser Pro
            100                 105                 110

His Thr Ala Val Lys Asp Phe Val Ile Ile Pro Leu His Thr Thr Pro
        115                 120                 125

Glu Thr Ser Val Lys Glu Ile Asp Glu Leu Val Glu Val Tyr Thr Asp
    130                 135                 140

Val Lys His Arg Trp Lys Ala Glu Asn Phe Ile Phe Met Gly Asp Phe
145                 150                 155                 160

Asn Ala Gly Cys Ser Tyr Val Pro Lys Lys Ala Trp Lys Asn Ile Arg
                165                 170                 175

Leu Arg Thr Asp Pro Arg Phe Val Trp Leu Ile Gly Asp Gln Glu Asp
            180                 185                 190

Thr Thr Val Lys Lys Ser Thr Asn Cys Ala Tyr Asp Arg Ile Val Leu
        195                 200                 205

Arg Gly Gln Glu Ile Val Ser Ser Val Pro Lys Ser Asn Ser Val
210                 215                 220

Phe Asp Phe Gln Lys Ala Tyr Lys Leu Thr Glu Glu Glu Ala Leu Asp
225                 230                 235                 240

Val Ser Asp His Phe Pro Val Glu Phe Lys Leu Gln Ser Ser Arg Ala
                245                 250                 255

Phe Thr Asn Ser Lys Lys Ser Val Thr Leu Arg Lys Lys Thr Lys Ser
            260                 265                 270

Lys Arg Ser
        275

<210> SEQ ID NO 6
<211> LENGTH: 360
<212> TYPE: PRT
<213> ORGANISM: Homo sapiens

<400> SEQUENCE: 6

Met Ile Pro Leu Leu Ala Ala Leu Leu Cys Val Pro Ala Gly Ala
1               5                   10                  15

Leu Thr Cys Tyr Gly Asp Ser Gly Gln Pro Val Asp Trp Phe Val Val
                20                  25                  30

Tyr Lys Leu Pro Ala Leu Arg Gly Ser Gly Glu Ala Ala Gln Arg Gly
            35                  40                  45

Leu Gln Tyr Lys Tyr Leu Asp Glu Ser Ser Gly Gly Trp Arg Asp Gly
        50                  55                  60

Arg Ala Leu Ile Asn Ser Pro Glu Gly Ala Val Gly Arg Ser Leu Gln
 65                  70                  75                  80

Pro Leu Tyr Arg Ser Asn Thr Ser Gln Leu Ala Phe Leu Leu Tyr Asn
                85                  90                  95

Asp Gln Pro Pro Gln Pro Ser Lys Ala Gln Asp Ser Ser Met Arg Gly
            100                 105                 110
```

His Thr Lys Gly Val Leu Leu Asp His Asp Gly Phe Trp Leu
            115                 120                 125

Val His Ser Val Pro Asn Phe Pro Pro Ala Ser Ala Ala Tyr
130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                    165                 170                 175

Thr Tyr Pro Trp Val Tyr Asn Tyr Gln Leu Glu Gly Ile Phe Ala Gln
                180                 185                 190

Glu Phe Pro Asp Leu Glu Asn Val Val Lys Gly His His Val Ser Gln
                195                 200                 205

Glu Pro Trp Asn Ser Ser Ile Thr Leu Thr Ser Gln Ala Gly Ala Val
210                 215                 220

Phe Gln Ser Phe Ala Lys Phe Ser Lys Phe Gly Asp Asp Leu Tyr Ser
225                 230                 235                 240

Gly Trp Leu Ala Ala Leu Gly Thr Asn Leu Gln Val Gln Phe Trp
                    245                 250                 255

His Lys Thr Val Gly Ile Leu Pro Ser Asn Cys Ser Asp Ile Trp Gln
                260                 265                 270

Val Leu Asn Val Asn Gln Ile Ala Phe Pro Gly Pro Ala Gly Pro Ser
275                 280                 285

Phe Asn Ser Thr Glu Asp His Ser Lys Trp Cys Val Ser Pro Lys Gly
290                 295                 300

Pro Trp Thr Cys Val Gly Asp Met Asn Arg Asn Gln Gly Glu Glu Gln
305                 310                 315                 320

Arg Gly Gly Thr Leu Cys Ala Gln Leu Pro Ala Leu Trp Lys Ala
                    325                 330                 335

Phe Gln Pro Leu Val Lys Asn Tyr Gln Pro Cys Asn Gly Met Ala Arg
                340                 345                 350

Lys Pro Ser Arg Ala Tyr Lys Ile
                355                 360

<210> SEQ ID NO 7
<211> LENGTH: 361
<212> TYPE: PRT
<213> ORGANISM: Homo sapiens

<400> SEQUENCE: 7

Met Lys Gln Lys Met Met Ala Arg Leu Leu Arg Thr Ser Phe Ala Leu
1               5                   10                  15

Leu Phe Leu Gly Leu Phe Gly Val Leu Gly Ala Ala Thr Ile Ser Cys
                20                  25                  30

Arg Asn Glu Glu Gly Lys Ala Val Asp Trp Phe Thr Phe Tyr Lys Leu
            35                  40                  45

Pro Lys Arg Gln Asn Lys Glu Ser Gly Glu Thr Gly Leu Glu Tyr Leu
        50                  55                  60

Tyr Leu Asp Ser Thr Thr Arg Ser Trp Arg Lys Ser Glu Gln Leu Met
65                  70                  75                  80

Asn Asp Thr Lys Ser Val Leu Gly Arg Thr Leu Gln Gln Leu Tyr Glu
                85                  90                  95

Ala Tyr Ala Ser Lys Ser Asn Asn Thr Ala Tyr Leu Ile Tyr Asn Asp
                100                 105                 110

Gly Val Pro Lys Pro Val Asn Tyr Ser Arg Lys Tyr Gly His Thr Lys
            115                 120                 125

Gly Leu Leu Leu Trp Asn Arg Val Gln Gly Phe Trp Leu Ile His Ser
    130                 135                 140

Ile Pro Gln Phe Pro Pro Ile Pro Glu Glu Gly Tyr Asp Tyr Pro Pro
145                 150                 155                 160

Thr Gly Arg Arg Asn Gly Gln Ser Gly Ile Cys Ile Thr Phe Lys Tyr
                165                 170                 175

Asn Gln Tyr Glu Ala Ile Asp Ser Gln Leu Leu Val Cys Asn Pro Asn
            180                 185                 190

Val Tyr Ser Cys Ser Ile Pro Ala Thr Phe His Gln Glu Leu Ile His
        195                 200                 205

Met Pro Gln Leu Cys Thr Arg Ala Ser Ser Glu Ile Pro Gly Arg
210                 215                 220

Leu Leu Thr Thr Leu Gln Ser Ala Gln Gly Gln Lys Phe Leu His Phe
225                 230                 235                 240

Ala Lys Ser Asp Ser Phe Leu Asp Asp Ile Phe Ala Ala Trp Met Ala
                245                 250                 255

Gln Arg Leu Lys Thr His Leu Leu Thr Glu Thr Trp Gln Arg Lys Arg
                260                 265                 270

Gln Glu Leu Pro Ser Asn Cys Ser Leu Pro Tyr His Val Tyr Asn Ile
            275                 280                 285

Lys Ala Ile Lys Leu Ser Arg His Ser Tyr Phe Ser Ser Tyr Gln Asp
290                 295                 300

His Ala Lys Trp Cys Ile Ser Gln Lys Gly Thr Lys Asn Arg Trp Thr
305                 310                 315                 320

Cys Ile Gly Asp Leu Asn Arg Ser Pro His Gln Ala Phe Arg Ser Gly
                325                 330                 335

Gly Phe Ile Cys Thr Gln Asn Trp Gln Ile Tyr Gln Ala Phe Gln Gly
            340                 345                 350

Leu Val Leu Tyr Tyr Glu Ser Cys Lys
            355                 360

<210> SEQ ID NO 8
<211> LENGTH: 304
<212> TYPE: PRT
<213> ORGANISM: Artificial Sequence
<220> FEATURE:
<223> OTHER INFORMATION: Synthetic Sequence

<400> SEQUENCE: 8

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

```
Val Phe Ser Arg Glu Pro Phe Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                    165                 170                 175

His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205

Thr Asp Pro Arg Phe Val Trp Leu Ile Gly Asp Gln Glu Asp Thr Thr
210                 215                 220

Ala Thr Pro Thr Asn Cys Ala Tyr Asp Arg Ile Val Leu Arg Gly Gln
225                 230                 235                 240

Glu Ile Val Ser Ser Val Val Pro Lys Ser Asn Ser Val Phe Asp Phe
                245                 250                 255

Gln Lys Ala Tyr Lys Leu Thr Glu Glu Ala Leu Asp Val Ser Asp
                260                 265                 270

His Phe Pro Val Glu Lys Leu Gln Ser Ser Arg Ala Phe Thr Asn
    275                 280                 285

Ser Lys Lys Ser Val Thr Leu Arg Lys Lys Thr Lys Ser Lys Arg Ser
290                 295                 300

<210> SEQ ID NO 9
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 9

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
        50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
                180                 185                 190
```

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
210                 215                 220

Val Lys Lys Ser Thr His Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
                260                 265                 270

Asp His Phe Pro Val Glu Phe Lys Leu Gln Ser Ser Arg Ala Phe Thr
                275                 280                 285

Asn Ser Lys Lys Ser Val Thr Leu Arg Lys Lys Thr Lys Ser Lys Arg
            290                 295                 300

Ser
305

<210> SEQ ID NO 10
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 10

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Val Ala Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305

<210> SEQ ID NO 11
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 11

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Met Leu Leu Arg Gly Ala Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
            290                 295                 300

Ser
305

<210> SEQ ID NO 12
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 12

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Asp Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
            290                 295                 300

Ser
305

<210> SEQ ID NO 13

```
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 13

Met Ser Arg Glu Leu Ala Pro Leu Leu Leu Leu Leu Ser Ile His
 1               5                  10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Asn Ser Arg
 65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
                100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ala Leu Pro Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305

<210> SEQ ID NO 14
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 14

Met Ser Arg Glu Leu Ala Pro Leu Leu Leu Leu Leu Ser Ile His
```

```
1               5                   10                  15
Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asn
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
            290                 295                 300

Ser
305

<210> SEQ ID NO 15
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 15

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
```

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Ala Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305

<210> SEQ ID NO 16
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 16

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser

```
                    100                 105                 110
Val Lys Arg Ser Tyr His Tyr His Asp Tyr Gln Asp Gly Asp Ala Asp
                115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Gly Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
    290                 295                 300

Ser
305

<210> SEQ ID NO 17
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 17

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
```

```
145                 150                 155                 160
Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205

Thr Asp Pro Arg Phe Val Trp Leu Ile Gly Asp Gln Glu Asp Thr Thr
            210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Ser Asp Gln Leu Ala Leu Asp Val Ser
                260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
            290                 295                 300

Ser
305
```

<210> SEQ ID NO 18
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 18

```
Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
                35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
                100                 105                 110

Val Lys Arg Ser Tyr His Tyr His Asp Tyr Gln Asp Gly Asp Ala Asp
                115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205
```

```
                     195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Gln Ala Ile Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
290                 295                 300

Ser
305

<210> SEQ ID NO 19
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 19

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
        50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
```

```
                    245                 250                 255

Phe Gln Lys Ala Tyr Lys Leu Thr Glu Glu Ala Leu Asp Val Ser
            260                 265                 270

Asp His Tyr Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
290                 295                 300

Ser
305

<210> SEQ ID NO 20
<211> LENGTH: 305
<212> TYPE: PRT
<213> ORGANISM: Artificial Sequence
<220> FEATURE:
<223> OTHER INFORMATION: Synthetic Sequence

<400> SEQUENCE: 20

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Val Met Leu Gln Ser Ser Arg Ala Phe Thr
            275                 280                 285

Asn Ser Lys Lys Ser Val Thr Leu Arg Lys Lys Thr Lys Ser Lys Arg
290                 295                 300
```

Ser
305

<210> SEQ ID NO 21
<211> LENGTH: 282
<212> TYPE: PRT
<213> ORGANISM: Artificial Sequence
<220> FEATURE:
<223> OTHER INFORMATION: Synthetic Sequence

<400> SEQUENCE: 21

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Lys
        275                 280

<210> SEQ ID NO 22
<211> LENGTH: 304
<212> TYPE: PRT
<213> ORGANISM: Homo sapiens

<400> SEQUENCE: 22

Met Ser Arg Glu Leu Ala Pro Leu Leu Leu Leu Leu Ser Ile His
1               5                   10                  15

```
Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
    275                 280                 285

Asn Ser Lys Lys Ser Val Thr Leu Arg Lys Lys Thr Lys Ser Lys Arg
290                 295                 300

<210> SEQ ID NO 23
<211> LENGTH: 302
<212> TYPE: PRT
<213> ORGANISM: Homo sapiens

<400> SEQUENCE: 23

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
```

```
            85                  90                  95
Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205

Thr Asp Pro Arg Phe Val Trp Leu Ile Gly Asp Gln Glu Asp Thr Thr
            210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
                260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser
            290                 295                 300

<210> SEQ ID NO 24
<211> LENGTH: 293
<212> TYPE: PRT
<213> ORGANISM: Homo sapiens

<400> SEQUENCE: 24

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
            50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160
```

-continued

```
Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser
    290

<210> SEQ ID NO 25
<211> LENGTH: 290
<212> TYPE: PRT
<213> ORGANISM: Homo sapiens

<400> SEQUENCE: 25

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240
```

```
Gln Glu Ile Val Ser Ser Val Pro Lys Ser Asn Ser Val Phe Asp
            245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
            275                 280                 285

Asn Ser
    290

<210> SEQ ID NO 26
<211> LENGTH: 284
<212> TYPE: PRT
<213> ORGANISM: Homo sapiens

<400> SEQUENCE: 26

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
            210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
            245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser
            275                 280

<210> SEQ ID NO 27
<211> LENGTH: 282
<212> TYPE: PRT
```

<213> ORGANISM: Homo sapiens

<400> SEQUENCE: 27

Met Ser Arg Glu Leu Ala Pro Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln
        275                 280

<210> SEQ ID NO 28
<211> LENGTH: 81
<212> TYPE: PRT
<213> ORGANISM: Artificial Sequence
<220> FEATURE:
<223> OTHER INFORMATION: Synthetic Sequence

<400> SEQUENCE: 28

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

```
Phe Ile Asn Thr Thr Ile Ala Ser Ile Ala Ala Lys Glu Glu Gly Val
 65                  70                  75                  80

Ser

<210> SEQ ID NO 29
<211> LENGTH: 24
<212> TYPE: PRT
<213> ORGANISM: Homo sapiens

<400> SEQUENCE: 29

Met Lys Trp Val Thr Phe Ile Ser Leu Leu Phe Leu Phe Ser Ser Ala
  1               5                  10                  15

Tyr Ser Arg Gly Val Phe Arg Arg
             20

<210> SEQ ID NO 30
<211> LENGTH: 20
<212> TYPE: PRT
<213> ORGANISM: Homo sapiens

<400> SEQUENCE: 30

Met Ser Arg Glu Leu Ala Pro Leu Leu Leu Leu Leu Leu Ser Ile His
  1               5                  10                  15

Ser Ala Leu Ala
             20

<210> SEQ ID NO 31
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 31

Gly Gly Gly Gly Ser
  1               5

<210> SEQ ID NO 32
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 32

Gly Gly Gly Gly Ser Gly Gly Gly Gly Ser Gly Gly Gly Gly Ser
  1               5                  10                  15

<210> SEQ ID NO 33
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 33

Ala Pro Ala Pro Ala Pro Ala Pro Ala Pro Ala Pro Ala Pro
  1               5                  10

<210> SEQ ID NO 34
<211> LENGTH: 12
<212> TYPE: PRT
<213> ORGANISM: Artificial Sequence
<220> FEATURE:
```

```
<223> OTHER INFORMATION: Synthetic Sequence

<400> SEQUENCE: 34

Ala Glu Ala Ala Ala Lys Glu Ala Ala Ala Lys Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 35

Ser Gly Gly Ser Gly Ser Ser
1               5

<210> SEQ ID NO 36
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 36

Ser Gly Gly Ser Gly Gly Ser Gly Gly Ser Gly Gly Ser Gly Ser Ser
1               5                   10                  15

<210> SEQ ID NO 37
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 37

Ser Gly Gly Ser Gly Gly Ser Gly Gly Ser Gly Gly Ser Gly Gly Ser
1               5                   10                  15

Gly Gly Ser Gly Gly Ser Gly Gly Ser Gly Gly Ser Gly Ser Ser
                20                  25                  30

<210> SEQ ID NO 38
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 38

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Ser
                20                  25

<210> SEQ ID NO 39
<211> LENGTH: 585
<212> TYPE: PRT
<213> ORGANISM: Homo sapiens

<400> SEQUENCE: 39

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30
```

-continued

```
Gln Cys Pro Phe Glu Asp His Val Lys Leu Val Asn Glu Val Thr Glu
         35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
                100                 105                 110
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
```

```
                450           455           460
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 40
<211> LENGTH: 625
<212> TYPE: PRT
<213> ORGANISM: Homo sapiens

<400> SEQUENCE: 40

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
            35                  40                  45

Val Cys Thr Tyr His Pro Arg Cys Leu Leu Phe Thr Phe Thr Ala Glu
        50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
            85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
            165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
210                 215                 220

Val Cys Gly Arg Ile Cys Thr His His Pro Gly Cys Leu Phe Phe Thr
225                 230                 235                 240
```

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
260                 265                 270

Lys Ala Leu Ser Gly Phe Ser Leu Gln Ser Cys Arg His Ser Ile Pro
            275                 280                 285

Val Phe Cys His Ser Ser Phe Tyr His Asp Thr Asp Phe Leu Gly Glu
290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Ile Ser Gly
        355                 360                 365

Tyr Thr Leu Arg Leu Cys Lys Met Asp Asn Glu Cys Thr Thr Lys Ile
370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
            500                 505                 510

Asp Cys Trp Val Thr Gly Trp Gly Tyr Arg Lys Leu Arg Asp Lys Ile
        515                 520                 525

Gln Asn Thr Leu Gln Lys Ala Lys Ile Pro Leu Val Thr Asn Glu Glu
530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
610                 615                 620

Val
625

<210> SEQ ID NO 41
<211> LENGTH: 638
<212> TYPE: PRT

<213> ORGANISM: Homo sapiens

<400> SEQUENCE: 41

```
Met Ile Leu Phe Lys Gln Ala Thr Tyr Phe Ile Ser Leu Phe Ala Thr
1               5                   10                  15
Val Ser Cys Gly Cys Leu Thr Gln Leu Tyr Glu Asn Ala Phe Phe Arg
            20                  25                  30
Gly Gly Asp Val Ala Ser Met Tyr Thr Pro Asn Ala Gln Tyr Cys Gln
        35                  40                  45
Met Arg Cys Thr Phe His Pro Arg Cys Leu Leu Phe Ser Phe Leu Pro
    50                  55                  60
Ala Ser Ser Ile Asn Asp Met Glu Lys Arg Phe Gly Cys Phe Leu Lys
65                  70                  75                  80
Asp Ser Val Thr Gly Thr Leu Pro Lys Val His Arg Thr Gly Ala Val
                85                  90                  95
Ser Gly His Ser Leu Lys Gln Cys Gly His Gln Ile Ser Ala Cys His
            100                 105                 110
Arg Asp Ile Tyr Lys Gly Val Asp Met Arg Gly Val Asn Phe Asn Val
        115                 120                 125
Ser Lys Val Ser Ser Val Glu Glu Cys Gln Lys Arg Cys Thr Asn Asn
    130                 135                 140
Ile Arg Cys Gln Phe Phe Ser Tyr Ala Thr Gln Thr Phe His Lys Ala
145                 150                 155                 160
Glu Tyr Arg Asn Asn Cys Leu Leu Lys Tyr Ser Pro Gly Gly Thr Pro
                165                 170                 175
Thr Ala Ile Lys Val Leu Ser Asn Val Glu Ser Gly Phe Ser Leu Lys
            180                 185                 190
Pro Cys Ala Leu Ser Glu Ile Gly Cys His Met Asn Ile Phe Gln His
        195                 200                 205
Leu Ala Phe Ser Asp Val Asp Val Ala Arg Val Leu Thr Pro Asp Ala
    210                 215                 220
Phe Val Cys Arg Thr Ile Cys Thr Tyr His Pro Asn Cys Leu Phe Phe
225                 230                 235                 240
Thr Phe Tyr Thr Asn Val Trp Lys Ile Glu Ser Gln Arg Asn Val Cys
                245                 250                 255
Leu Leu Lys Thr Ser Glu Ser Gly Thr Pro Ser Ser Ser Thr Pro Gln
            260                 265                 270
Glu Asn Thr Ile Ser Gly Tyr Ser Leu Leu Thr Cys Lys Arg Thr Leu
        275                 280                 285
Pro Glu Pro Cys His Ser Lys Ile Tyr Pro Gly Val Asp Phe Gly Gly
    290                 295                 300
Glu Glu Leu Asn Val Thr Phe Val Lys Gly Val Asn Val Cys Gln Glu
305                 310                 315                 320
Thr Cys Thr Lys Met Ile Arg Cys Gln Phe Phe Thr Tyr Ser Leu Leu
                325                 330                 335
Pro Glu Asp Cys Lys Glu Glu Lys Cys Lys Cys Phe Leu Arg Leu Ser
            340                 345                 350
Met Asp Gly Ser Pro Thr Arg Ile Ala Tyr Gly Thr Gln Gly Ser Ser
        355                 360                 365
Gly Tyr Ser Leu Arg Leu Cys Asn Thr Gly Asp Asn Ser Val Cys Thr
    370                 375                 380
Thr Lys Thr Ser Thr Arg Ile Val Gly Gly Thr Asn Ser Ser Trp Gly
385                 390                 395                 400
```

```
Glu Trp Pro Trp Gln Val Ser Leu Gln Val Lys Leu Thr Ala Gln Arg
                405                 410                 415
His Leu Cys Gly Gly Ser Leu Ile Gly His Gln Trp Val Leu Thr Ala
            420                 425                 430
Ala His Cys Phe Asp Gly Leu Pro Leu Gln Asp Val Trp Arg Ile Tyr
        435                 440                 445
Ser Gly Ile Leu Asn Leu Ser Asp Ile Thr Lys Asp Thr Pro Phe Ser
    450                 455                 460
Gln Ile Lys Glu Ile Ile Ile His Gln Asn Tyr Lys Val Ser Glu Gly
465                 470                 475                 480
Asn His Asp Ile Ala Leu Ile Lys Leu Gln Ala Pro Leu Asn Tyr Thr
                485                 490                 495
Glu Phe Gln Lys Pro Ile Cys Leu Pro Ser Lys Gly Asp Thr Ser Thr
            500                 505                 510
Ile Tyr Thr Asn Cys Trp Val Thr Gly Trp Gly Phe Ser Lys Glu Lys
        515                 520                 525
Gly Glu Ile Gln Asn Ile Leu Gln Lys Val Asn Ile Pro Leu Val Thr
    530                 535                 540
Asn Glu Glu Cys Gln Lys Arg Tyr Gln Asp Tyr Lys Ile Thr Gln Arg
545                 550                 555                 560
Met Val Cys Ala Gly Tyr Lys Glu Gly Lys Asp Ala Cys Lys Gly
                565                 570                 575
Asp Ser Gly Gly Pro Leu Val Cys Lys His Asn Gly Met Trp Arg Leu
            580                 585                 590
Val Gly Ile Thr Ser Trp Gly Glu Gly Cys Ala Arg Arg Glu Gln Pro
        595                 600                 605
Gly Val Tyr Thr Lys Val Ala Glu Tyr Met Asp Trp Ile Leu Glu Lys
    610                 615                 620
Thr Gln Ser Ser Asp Gly Lys Ala Gln Met Gln Ser Pro Ala
625                 630                 635

<210> SEQ ID NO 42
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 42

Met Gly Asp Phe Asn Ala Gly Cys Ser Tyr Val
1               5                   10

<210> SEQ ID NO 43
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 43

Cys Thr Thr Lys Ile Lys Pro Arg Ile Val Gly Gly Thr Ala Ser Val
1               5                   10                  15
Arg Gly Glu Trp Pro Trp Gln Val Thr
            20                  25

<210> SEQ ID NO 44
<211> LENGTH: 13
<212> TYPE: PRT
<213> ORGANISM: Artificial Sequence
```

<220> FEATURE:
<223> OTHER INFORMATION: Synthetic Sequence

<400> SEQUENCE: 44

Gly Gly Gly Gly Ser Pro Arg Ile Gly Gly Gly Ser
1               5                   10

<210> SEQ ID NO 45
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 45

Val Cys Thr Thr Lys Thr Ser Thr Arg Ile Val Gly Gly Thr Asn Ser
1               5                   10                  15

Ser Trp Gly Glu Trp Pro Trp Gln Val Ser
            20                  25

<210> SEQ ID NO 46
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 46

Ser Thr Arg Ile Val Gly Gly
1               5

<210> SEQ ID NO 47
<211> LENGTH: 878
<212> TYPE: PRT
<213> ORGANISM: Artificial Sequence
<220> FEATURE:
<223> OTHER INFORMATION: Synthetic Sequence

<400> SEQUENCE: 47

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

```
Cys Leu Leu Pro Lys Leu Asp Glu Leu Arg Asp Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
    275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
        340                 345                 350

Tyr Glu Thr Thr Leu Glu Lys Cys Cys Ala Ala Ala Asp Pro His Glu
    355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ser Gly Gly Ser Gly Gly Ser
        580                 585                 590
```

```
Gly Gly Ser Gly Gly Ser Gly Ser Gly Gly Ser Gly Gly Ser Gly
            595                 600             605
Gly Ser Gly Gly Ser Gly Ser Ser Met Arg Ile Cys Ser Phe Asn Val
    610                 615                 620
Arg Ser Phe Gly Glu Ser Lys Gln Glu Asp Lys Asn Ala Met Asp Val
625                 630                 635                 640
Ile Val Lys Val Ile Lys Arg Cys Asp Ile Ile Leu Val Met Glu Ile
                645                 650                 655
Lys Asp Ser Asn Asn Arg Ile Cys Pro Ile Leu Met Glu Lys Leu Asn
            660                 665                 670
Arg Asn Ser Arg Arg Gly Ile Thr Tyr Asn Tyr Val Ile Ser Ser Arg
            675                 680                 685
Leu Gly Arg Asn Thr Tyr Lys Glu Gln Tyr Ala Phe Leu Tyr Lys Glu
    690                 695                 700
Lys Leu Val Ser Val Lys Arg Ser Tyr His Tyr His Asp Tyr Gln Asp
705                 710                 715                 720
Gly Asp Ala Asp Val Phe Ser Arg Glu Pro Phe Val Val Trp Phe Gln
                725                 730                 735
Ser Pro His Thr Ala Val Lys Asp Phe Val Ile Ile Pro Leu His Thr
            740                 745                 750
Thr Pro Glu Thr Ser Val Lys Glu Ile Asp Glu Leu Val Glu Val Tyr
            755                 760                 765
Thr Asp Val Lys His Arg Trp Lys Ala Glu Asn Phe Ile Phe Met Gly
    770                 775                 780
Asp Phe Asn Ala Gly Cys Ser Tyr Val Pro Lys Lys Ala Trp Lys Asn
785                 790                 795                 800
Ile Arg Leu Arg Thr Asp Pro Arg Phe Val Trp Leu Ile Gly Asp Gln
                805                 810                 815
Glu Asp Thr Thr Val Lys Lys Ser Thr Asn Cys Ala Tyr Asp Arg Ile
            820                 825                 830
Val Leu Arg Gly Gln Glu Ile Val Ser Ser Val Val Pro Lys Ser Asn
            835                 840                 845
Ser Val Phe Asp Phe Gln Lys Ala Tyr Lys Leu Thr Glu Glu Glu Ala
    850                 855                 860
Leu Asp Val Ser Asp His Phe Pro Val Glu Phe Lys Leu Gln
865                 870                 875
```